United States Patent
Cordoba et al.

(10) Patent No.: US 11,959,084 B2
(45) Date of Patent: Apr. 16, 2024

(54) NUCLEIC ACID CONSTRUCT

(71) Applicant: AUTOLUS LIMITED, London (GB)

(72) Inventors: Shaun Cordoba, London (GB); James Sillibourne, London (GB); Martin Pulé, London (GB)

(73) Assignee: AUTOLUS LIMITED, London (GB)

(*) Notice: Subject to any disclaimer, the term of this patent is extended or adjusted under 35 U.S.C. 154(b) by 637 days.

(21) Appl. No.: 17/254,001

(22) PCT Filed: Jul. 31, 2019

(86) PCT No.: PCT/GB2019/052150
§ 371 (c)(1),
(2) Date: Dec. 18, 2020

(87) PCT Pub. No.: WO2020/025953
PCT Pub. Date: Feb. 6, 2020

(65) Prior Publication Data
US 2022/0106602 A1 Apr. 7, 2022

(30) Foreign Application Priority Data

Jul. 31, 2018 (GB) .................................... 1812474

(51) Int. Cl.
*C12N 15/67* (2006.01)
*C07K 14/705* (2006.01)
*C07K 14/725* (2006.01)

(52) U.S. Cl.
CPC ........ *C12N 15/67* (2013.01); *C07K 14/70503* (2013.01); *C07K 14/7051* (2013.01); *C07K 2319/02* (2013.01); *C07K 2319/03* (2013.01)

(58) Field of Classification Search
None
See application file for complete search history.

(56) References Cited

FOREIGN PATENT DOCUMENTS

| WO | WO-9014422 A1 | 11/1990 |
|---|---|---|
| WO | WO-2005/017133 A1 | 2/2005 |
| WO | WO-2011/048353 A2 | 4/2011 |
| WO | WO-2013153391 A1 | 10/2013 |
| WO | WO-2015/132604 A1 | 9/2015 |
| WO | WO-2016174409 A1 | 11/2016 |
| WO | WO-2017029512 A1 | 2/2017 |
| WO | WO-2018/208856 A1 | 11/2018 |
| WO | WO-2020183131 A1 | 9/2020 |

OTHER PUBLICATIONS

Sillibourne, et al. (2022) "A compact and simple method of achieving differential transgene expression by exploiting translational readthrough", BioTechniques, 72(4): 143-54.*
Shingu et al., "Conferring Cadmium Resistance to Mature Tobacco Plants Through Metal-Adsorbing Particles of Tomato Mosaic Virus Vector," Plant Biotechnology Journal, 4:281-288 (2006).
Choi Min-Yeon et al: "Adjustable under-expression of yeast mating pathway proteins in Saccharomyces cerevisiae using a programmed ribosomal frameshift", Applied Microbiology and Biotechnology, vol. 100, No. 11, Feb. 2, 2016, pp. 4997-50005, XP035870432.
Fan Yongqiang et al: "Heterogeneity of Stop Codon Readthrough in Single Bacterial Cells and Implications for Population Fitness", Molecular Cell, vol. 67, No. 5, Aug. 3, 2017, p. 826, XP085189875.
Gary Loughran et al: "Stop codon readthrough generates a C-terminally extended variant of the human vitamin D receptor with reduced calcitriol response", Journal of Biological Chemistry, vol. 293, No. 12, Jan. 31, 2018, pp. 44344-4444, XP055663443.
Donelly et al: "The 'cleavage' activities of foot-and-mouth disease virus 2A site-directed mutants and naturally occurring '2A-like' sequences", Journal of General Virology (2001, vol. 82, pp. 1027-1041.
Written Opinion of the International Search Authority for International Application No. PCT/GB2019/052150 dated Feb. 14, 2020.
Wons E., et al., "RNA Editing by T7 RNA Polymerase Bypasses InDel Mutations Causing Unexpected Phenotypic Changes", Nucleic Acids Research, 2015, vol. 43, No. 8, pp. 3950-3963, DOI: 10.1093/nar/gkv269.
Donnelly et al., "Analysis of the Aphthovirus 2A/2B Polyprotein 'Cleavage' Mechanism Indicates not a Proteolytic Reaction, but a Novel Translational Effect: A Putative Ribosomal 'Skip',", Journal of General Virology, 82(5):1013-1025 (2001).
International Search Report from International Application No. PCT/GB2019/052150, dated Feb. 12, 2020, 8 pages.
Thoms, Neue Isoformen für alte Enzyme Durch Translationalen readthrough, "New isoforms for old enzymes through translational readthrough," Bio-Spectrum, Spectrum Academic Publishers, DE, vol. 23, No. 5, Oct. 11, 2017, XP036336124, pp. 506-509, doi:10.1007/S12268-017-0830-4, ISSN 0947-0867 (Two different machine translations are submitted herewith).

* cited by examiner

*Primary Examiner* — Robert M Kelly
(74) *Attorney, Agent, or Firm* — MARSHALL, GERSTEIN & BORUN LLP

(57) ABSTRACT

The present invention provides a nucleic acid construct comprising: a first nucleotide sequence of interest (NOI1); a frame-slip motif or a translational readthrough motif (FSM/TRM); and a second nucleotide sequence of interest (NOI2). The invention also provides vectors and cells expressing such a construct. The invention also provides a method for modulating the relative expression of two transgenes in a nucleic acid construct which comprises the step of including a frame-slip motif or a translational readthrough motif between the two transgenes in order to reduce the expression of the downstream transgene.

21 Claims, 14 Drawing Sheets
Specification includes a Sequence Listing.

(a)

(b)

(c)

A

Readthrough STOP-CUAG    Readthrough STOP-CAAUUA
   UGA-CUAG                  UGA-CAAUUA
   UAG-CUAG                  UAG-CAAUUA
   UAA-CUAG                  UAA-CAAUUA

B

B'

C

D

E

E'

F

F'

SEQUENCE LISTING

```
<160> NUMBER OF SEQ ID NOS: 59

<210> SEQ ID NO 1
<211> LENGTH: 7
<212> TYPE: DNA
<213> ORGANISM: Artificial Sequence
<220> FEATURE:
<223> OTHER INFORMATION: frame-slip motif

<400> SEQUENCE: 1 uuuuuuu                                                              7

<210> SEQ ID NO 2
<211> LENGTH: 9
<212> TYPE: DNA
<213> ORGANISM: Artificial Sequence
<220> FEATURE:
<223> OTHER INFORMATION: frame-slip motif

<400> SEQUENCE: 2 uuuuuuuga                                                            9

<210> SEQ ID NO 3
<211> LENGTH: 9
<212> TYPE: DNA
<213> ORGANISM: Artificial Sequence
<220> FEATURE:
<223> OTHER INFORMATION: frame-slip motif

<400> SEQUENCE: 3 uuuuuuuag                                                            9

<210> SEQ ID NO 4
<211> LENGTH: 9
<212> TYPE: DNA
<213> ORGANISM: Artificial Sequence
<220> FEATURE:
```

```
<223> OTHER INFORMATION: frame-slip motif

<400> SEQUENCE: 4 uuuuuuuaa                                                                          9

<210> SEQ ID NO 5
<211> LENGTH: 7
<212> TYPE: DNA
<213> ORGANISM: Artificial Sequence
<220> FEATURE:
<223> OTHER INFORMATION: translational readthrough motif

<400> SEQUENCE: 5 ugacuag                                                                            7

<210> SEQ ID NO 6
<211> LENGTH: 7
<212> TYPE: DNA
<213> ORGANISM: Artificial Sequence
<220> FEATURE:
<223> OTHER INFORMATION: translational readthrough motif

<400> SEQUENCE: 6 uagcuag                                                                            7

<210> SEQ ID NO 7
<211> LENGTH: 7
<212> TYPE: DNA
<213> ORGANISM: Artificial Sequence
<220> FEATURE:
<223> OTHER INFORMATION: translational readthrough motif

<400> SEQUENCE: 7 uaacuag                                                                            7

<210> SEQ ID NO 8
<211> LENGTH: 9
<212> TYPE: DNA
<213> ORGANISM: Artificial Sequence
<220> FEATURE:
<223> OTHER INFORMATION: translational readthrough motif

<400> SEQUENCE: 8 ugacaauua                                                                          9

<210> SEQ ID NO 9
<211> LENGTH: 9
<212> TYPE: DNA
<213> ORGANISM: Artificial Sequence
<220> FEATURE:
<223> OTHER INFORMATION: translational readthrough motif

<400> SEQUENCE: 9 uagcaauua                                                                          9

<210> SEQ ID NO 10
<211> LENGTH: 9
<212> TYPE: DNA
<213> ORGANISM: Artificial Sequence
<220> FEATURE:
<223> OTHER INFORMATION: translational readthrough motif

<400> SEQUENCE: 10 uaacaauua                                                                          9
```

```
<210> SEQ ID NO 11
<211> LENGTH: 10
<212> TYPE: DNA
<213> ORGANISM: Artificial Sequence
<220> FEATURE:
<223> OTHER INFORMATION: multiple stop translational readthrough motif

<400> SEQUENCE: 11
ugaugacuag                                                          10

<210> SEQ ID NO 12
<211> LENGTH: 8
<212> TYPE: PRT
<213> ORGANISM: Artificial Sequence
<220> FEATURE:
<223> OTHER INFORMATION: cleavage site motif

<400> SEQUENCE: 12

Asp Met Glu Ser Asn Pro Gly Pro
1               5

<210> SEQ ID NO 13
<211> LENGTH: 8
<212> TYPE: PRT
<213> ORGANISM: Artificial Sequence
<220> FEATURE:
<223> OTHER INFORMATION: cleavage site motif

<400> SEQUENCE: 13

Asp Val Glu Leu Asn Pro Gly Pro
1               5

<210> SEQ ID NO 14
<211> LENGTH: 8
<212> TYPE: PRT
<213> ORGANISM: Artificial Sequence
<220> FEATURE:
<223> OTHER INFORMATION: cleavage site motif

<400> SEQUENCE: 14

Asp Val Glu Glu Asn Pro Gly Pro
1               5

<210> SEQ ID NO 15
<211> LENGTH: 8
<212> TYPE: PRT
<213> ORGANISM: Artificial Sequence
<220> FEATURE:
<223> OTHER INFORMATION: cleavage site motif

<400> SEQUENCE: 15

Asp Ile Glu Leu Asn Pro Gly Pro
1               5

<210> SEQ ID NO 16
<211> LENGTH: 8
<212> TYPE: PRT
<213> ORGANISM: Artificial Sequence
<220> FEATURE:
<223> OTHER INFORMATION: cleavage site motif

<400> SEQUENCE: 16

Asp Ile Glu Gln Asn Pro Gly Pro
1               5

<210> SEQ ID NO 17
<211> LENGTH: 8
```

```
<212> TYPE: PRT
<213> ORGANISM: Artificial Sequence
<220> FEATURE:
<223> OTHER INFORMATION: cleavage site motif

<400> SEQUENCE: 17

Asp Ser Glu Phe Asn Pro Gly Pro
1               5

<210> SEQ ID NO 18
<211> LENGTH: 19
<212> TYPE: PRT
<213> ORGANISM: Artificial Sequence
<220> FEATURE:
<223> OTHER INFORMATION: cleavage sequence

<400> SEQUENCE: 18

Leu Leu Asn Phe Asp Leu Leu Lys Leu Ala Gly Asp Val Glu Ser Asn
1               5                   10                  15

Pro Gly Pro

<210> SEQ ID NO 19
<211> LENGTH: 19
<212> TYPE: PRT
<213> ORGANISM: Artificial Sequence
<220> FEATURE:
<223> OTHER INFORMATION: cleavage sequence

<400> SEQUENCE: 19

Leu Leu Asn Phe Asp Leu Leu Lys Leu Ala Gly Asp Val Gln Ser Asn
1               5                   10                  15

Pro Gly Pro

<210> SEQ ID NO 20
<211> LENGTH: 19
<212> TYPE: PRT
<213> ORGANISM: Artificial Sequence
<220> FEATURE:
<223> OTHER INFORMATION: cleavage sequence

<400> SEQUENCE: 20

Leu Leu Asn Phe Asp Leu Leu Lys Leu Ala Gly Asp Val Glu Ile Asn
1               5                   10                  15

Pro Gly Pro

<210> SEQ ID NO 21
<211> LENGTH: 19
<212> TYPE: PRT
<213> ORGANISM: Artificial Sequence
<220> FEATURE:
<223> OTHER INFORMATION: cleavage sequence

<400> SEQUENCE: 21

Leu Leu Asn Phe Asp Leu Leu Lys Leu Ala Gly Asp Val Glu Phe Asn
1               5                   10                  15

Pro Gly Pro

<210> SEQ ID NO 22
<211> LENGTH: 19
<212> TYPE: PRT
<213> ORGANISM: Artificial Sequence
<220> FEATURE:
<223> OTHER INFORMATION: cleavage sequence

<400> SEQUENCE: 22
```

```
Leu Leu Asn Phe Asp Leu Leu Lys Leu Ala Gly Asp Val Glu Ser His
1               5                   10                  15

Pro Gly Pro

<210> SEQ ID NO 23
<211> LENGTH: 19
<212> TYPE: PRT
<213> ORGANISM: Artificial Sequence
<220> FEATURE:
<223> OTHER INFORMATION: cleavage sequence

<400> SEQUENCE: 23

Leu Leu Asn Phe Asp Leu Leu Lys Leu Ala Gly Asp Val Glu Ser Glu
1               5                   10                  15

Pro Gly Pro

<210> SEQ ID NO 24
<211> LENGTH: 19
<212> TYPE: PRT
<213> ORGANISM: Artificial Sequence
<220> FEATURE:
<223> OTHER INFORMATION: cleavage sequence

<400> SEQUENCE: 24

Leu Leu Asn Phe Asp Leu Leu Lys Leu Ala Gly Asp Val Glu Ser Gln
1               5                   10                  15

Pro Gly Pro

<210> SEQ ID NO 25
<211> LENGTH: 19
<212> TYPE: PRT
<213> ORGANISM: Artificial Sequence
<220> FEATURE:
<223> OTHER INFORMATION: cleavage sequence

<400> SEQUENCE: 25

Leu Leu Asn Phe Asp Leu Leu Lys Leu Ala Gly Asp Val Glu Ser Asn
1               5                   10                  15

Pro Gly Gly

<210> SEQ ID NO 26
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 26

Tyr His Ala Asp Tyr Tyr Lys Gln Arg Leu Ile His Asp Val Glu Met
1               5                   10                  15

Asn Pro Gly Pro
            20

<210> SEQ ID NO 27
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 27

His Tyr Ala Gly Tyr Phe Ala Asp Leu Leu Ile His Asp Ile Glu Thr
1               5                   10                  15
```

Asn Pro Gly Pro
            20

<210> SEQ ID NO 28
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 28

Gln Cys Thr Asn Tyr Ala Leu Leu Lys Leu Ala Gly Asp Val Glu Ser
1               5                   10                  15

Asn Pro Gly Pro
            20

<210> SEQ ID NO 29
<211> LENGTH: 19
<212> TYPE: PRT
<213> ORGANISM: Artificial Sequence
<220> FEATURE:
<223> OTHER INFORMATION: cleavage site, 2A-like sequence

<400> SEQUENCE: 29

Ala Thr Asn Phe Ser Leu Leu Lys Gln Ala Gly Asp Val Glu Glu Asn
1               5                   10                  15

Pro Gly Pro

<210> SEQ ID NO 30
<211> LENGTH: 19
<212> TYPE: PRT
<213> ORGANISM: Artificial Sequence
<220> FEATURE:
<223> OTHER INFORMATION: cleavage site, 2A-like sequence

<400> SEQUENCE: 30

Ala Ala Arg Gln Met Leu Leu Leu Leu Ser Gly Asp Val Glu Thr Asn
1               5                   10                  15

Pro Gly Pro

<210> SEQ ID NO 31
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 31

Arg Ala Glu Gly Arg Gly Ser Leu Leu Thr Cys Gly Asp Val Glu Glu
1               5                   10                  15

Asn Pro Gly Pro
            20

<210> SEQ ID NO 32
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 32

Thr Arg Ala Glu Ile Glu Asp Glu Leu Ile Arg Ala Gly Ile Glu Ser
1               5                   10                  15

Asn Pro Gly Pro
        20

<210> SEQ ID NO 33
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 33

Thr Arg Ala Glu Ile Glu Asp Glu Leu Ile Arg Ala Asp Ile Glu Ser
1               5                   10                  15

Asn Pro Gly Pro
        20

<210> SEQ ID NO 34
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 34

Ala Lys Phe Gln Ile Asp Lys Ile Leu Ile Ser Gly Asp Val Glu Leu
1               5                   10                  15

Asn Pro Gly Pro
        20

<210> SEQ ID NO 35
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 35

Ser Ser Ile Ile Arg Thr Lys Met Leu Val Ser Gly Asp Val Glu Glu
1               5                   10                  15

Asn Pro Gly Pro
        20

<210> SEQ ID NO 36
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 36

Cys Asp Ala Gln Arg Gln Lys Leu Leu Leu Ser Gly Asp Ile Glu Gln
1               5                   10                  15

Asn Pro Gly Pro
        20

<210> SEQ ID NO 37
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 37

Tyr Pro Ile Asp Phe Gly Gly Phe Leu Val Lys Ala Asp Ser Glu Phe
1               5                   10                  15

Asn Pro Gly Pro
          20

<210> SEQ ID NO 38
<211> LENGTH: 57
<212> TYPE: PRT
<213> ORGANISM: Artificial Sequence
<220> FEATURE:
<223> OTHER INFORMATION: cleavage sequence

<400> SEQUENCE: 38

Val Thr Glu Leu Leu Tyr Arg Met Lys Arg Ala Glu Thr Tyr Cys Pro
1               5                   10                  15

Arg Pro Leu Ala Ile His Pro Thr Glu Ala Arg His Lys Gln Lys Ile
            20                  25                  30

Val Ala Pro Val Lys Gln Thr Leu Asn Phe Asp Leu Leu Lys Leu Ala
        35                  40                  45

Gly Asp Val Glu Ser Asn Pro Gly Pro
    50                  55

<210> SEQ ID NO 39
<211> LENGTH: 40
<212> TYPE: PRT
<213> ORGANISM: Artificial Sequence
<220> FEATURE:
<223> OTHER INFORMATION: cleavage sequence

<400> SEQUENCE: 39

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 40
<211> LENGTH: 33
<212> TYPE: PRT
<213> ORGANISM: Artificial Sequence
<220> FEATURE:
<223> OTHER INFORMATION: cleavage sequence

<400> SEQUENCE: 40

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 41
<211> LENGTH: 24
<212> TYPE: PRT
<213> ORGANISM: Artificial Sequence
<220> FEATURE:
<223> OTHER INFORMATION: cleavage sequence

<400> SEQUENCE: 41

Ala Pro Val Lys Gln Thr Leu Asn Phe Asp Leu Leu Lys Leu Ala Gly
1               5                   10                  15

Asp Val Glu Ser Asn Pro Gly Pro
            20

```
<210> SEQ ID NO 42
<211> LENGTH: 20
<212> TYPE: PRT
<213> ORGANISM: Artificial Sequence
<220> FEATURE:
<223> OTHER INFORMATION: murine Ig kappa chain V-III region signal
      peptide (wild-type)

<400> SEQUENCE: 42

Met Glu Thr Asp Thr Leu Ile Leu Trp Val Leu Leu Leu Val Pro
1               5                   10                  15

Gly Ser Thr Gly
            20

<210> SEQ ID NO 43
<211> LENGTH: 20
<212> TYPE: PRT
<213> ORGANISM: Artificial Sequence
<220> FEATURE:
<223> OTHER INFORMATION: murine Ig kappa chain V-III region signal
      peptide (K9 mutant)

<400> SEQUENCE: 43

Met Glu Thr Asp Thr Leu Ile Leu Lys Val Leu Leu Leu Val Pro
1               5                   10                  15

Gly Ser Thr Gly
            20

<210> SEQ ID NO 44
<211> LENGTH: 20
<212> TYPE: PRT
<213> ORGANISM: Artificial Sequence
<220> FEATURE:
<223> OTHER INFORMATION: murine Ig kappa chain V-III region signal
      peptide (K10 mutant)

<400> SEQUENCE: 44

Met Glu Thr Asp Thr Leu Ile Leu Trp Lys Leu Leu Leu Val Pro
1               5                   10                  15

Gly Ser Thr Gly
            20

<210> SEQ ID NO 45
<211> LENGTH: 20
<212> TYPE: PRT
<213> ORGANISM: Artificial Sequence
<220> FEATURE:
<223> OTHER INFORMATION: murine Ig kappa chain V-III region signal
      peptide (K11 mutant)

<400> SEQUENCE: 45

Met Glu Thr Asp Thr Leu Ile Leu Trp Val Lys Leu Leu Leu Val Pro
1               5                   10                  15

Gly Ser Thr Gly
            20

<210> SEQ ID NO 46
<211> LENGTH: 8
<212> TYPE: PRT
<213> ORGANISM: Artificial Sequence
<220> FEATURE:
<223> OTHER INFORMATION: cleavage site motif

<400> SEQUENCE: 46

Asp Ile Glu Thr Asn Pro Gly Pro
```

```
1               5

<210> SEQ ID NO 47
<211> LENGTH: 8
<212> TYPE: PRT
<213> ORGANISM: Artificial Sequence
<220> FEATURE:
<223> OTHER INFORMATION: cleavage site motif

<400> SEQUENCE: 47

Asp Val Glu Thr Asn Pro Gly Pro
1               5

<210> SEQ ID NO 48
<211> LENGTH: 8
<212> TYPE: PRT
<213> ORGANISM: Artificial Sequence
<220> FEATURE:
<223> OTHER INFORMATION: cleavage site motif

<400> SEQUENCE: 48

Asp Val Glu Met Asn Pro Gly Pro
1               5

<210> SEQ ID NO 49
<211> LENGTH: 8
<212> TYPE: PRT
<213> ORGANISM: Artificial Sequence
<220> FEATURE:
<223> OTHER INFORMATION: cleavage site motif

<400> SEQUENCE: 49

Asp Val Glu Ser Asn Pro Gly Pro
1               5

<210> SEQ ID NO 50
<211> LENGTH: 4
<212> TYPE: PRT
<213> ORGANISM: Artificial Sequence
<220> FEATURE:
<223> OTHER INFORMATION: basic amino acid furin target sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa may be Arg or Lys

<400> SEQUENCE: 50

Arg Xaa Xaa Arg
1

<210> SEQ ID NO 51
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 51

Glu Asn Leu Tyr Phe Gln Ser
1               5

<210> SEQ ID NO 52
<211> LENGTH: 8
```

```
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (2)..(2)
<223> OTHER INFORMATION: Xaa may be any amino acid or may be selected
      from the group: I, V, M and S
<220> FEATURE:
<221> NAME/KEY: MISC_FEATURE
<222> LOCATION: (4)..(4)
<223> OTHER INFORMATION: Xaa may be any amino acid or may be selected
      from the group: T, M, S, L, E, Q and F

<400> SEQUENCE: 52

Asp Xaa Glu Xaa Asn Pro Gly Pro
1               5

<210> SEQ ID NO 53
<211> LENGTH: 197
<212> TYPE: PRT
<213> ORGANISM: Homo sapiens

<400> SEQUENCE: 53

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 54
<211> LENGTH: 304
<212> TYPE: PRT
<213> ORGANISM: Homo sapiens

<400> SEQUENCE: 54

Trp Glu Leu Lys Lys Asp Val Tyr Val Val Glu Leu Asp Trp Tyr Pro
1               5                   10                  15

Asp Ala Pro Gly Glu Met Val Val Leu Thr Cys Asp Thr Pro Glu Glu
```

-continued

```
                20                  25                  30
Asp Gly Ile Thr Trp Thr Leu Asp Gln Ser Ser Glu Val Leu Gly Ser
            35                  40                  45

Gly Lys Thr Leu Thr Ile Gln Val Lys Glu Phe Gly Asp Ala Gly Gln
        50                  55                  60
Tyr Thr Cys His Lys Gly Gly Glu Val Leu Ser His Ser Leu Leu Leu
65                  70                  75                  80
Leu His Lys Lys Glu Asp Gly Ile Trp Ser Thr Asp Ile Leu Lys Asp
                85                  90                  95
Gln Lys Glu Pro Lys Asn Lys Thr Phe Leu Arg Cys Glu Ala Lys Asn
            100                 105                 110
Tyr Ser Gly Arg Phe Thr Cys Trp Trp Leu Thr Thr Ile Ser Thr Asp
        115                 120                 125
Leu Thr Phe Ser Val Lys Ser Ser Arg Gly Ser Ser Asp Pro Gln Gly
    130                 135                 140
Val Thr Cys Gly Ala Ala Thr Leu Ser Ala Glu Arg Val Arg Gly Asp
145                 150                 155                 160
Asn Lys Glu Tyr Glu Tyr Ser Val Glu Cys Gln Glu Asp Ser Ala Cys
                165                 170                 175
Pro Ala Ala Glu Glu Ser Leu Pro Ile Glu Val Met Val Asp Ala Val
            180                 185                 190
His Lys Leu Lys Tyr Glu Asn Tyr Thr Ser Ser Phe Phe Ile Arg Asp
        195                 200                 205
Ile Ile Lys Pro Asp Pro Pro Lys Asn Leu Gln Leu Lys Pro Leu Lys
    210                 215                 220
Asn Ser Arg Gln Val Glu Val Ser Trp Glu Tyr Pro Asp Thr Trp Ser
225                 230                 235                 240
Thr Pro His Ser Tyr Phe Ser Leu Thr Phe Cys Val Gln Val Gln Gly
                245                 250                 255
Lys Ser Lys Arg Glu Lys Lys Asp Arg Val Phe Thr Asp Lys Thr Ser
            260                 265                 270
Ala Thr Val Ile Cys Arg Lys Asn Ala Ser Ile Ser Val Arg Ala Gln
        275                 280                 285
Asp Arg Tyr Tyr Ser Ser Ser Trp Ser Glu Trp Ala Ser Val Pro Cys
    290                 295                 300

<210> SEQ ID NO 55
<211> LENGTH: 540
<212> TYPE: PRT
<213> ORGANISM: Artificial Sequence
<220> FEATURE:
<223> OTHER INFORMATION: a flexi-IL-12 sequence

<400> SEQUENCE: 55

Met Glu Thr Asp Thr Leu Leu Leu Trp Val Leu Leu Leu Trp Val Pro
1               5                   10                  15
Gly Ser Thr Gly Met Trp Ile Trp Glu Leu Lys Lys Asp Val Tyr Val
            20                  25                  30
Val Glu Leu Asp Trp Tyr Pro Asp Ala Pro Gly Glu Met Val Val Leu
        35                  40                  45
Thr Cys Asp Thr Pro Glu Glu Asp Gly Ile Thr Trp Thr Leu Asp Gln
    50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Val
```

```
                85                  90                  95
Leu Ser His Ser Leu Leu Leu His Lys Lys Glu Asp Gly Ile Trp
            100                 105                 110
Ser Thr Asp Ile Leu Lys Asp Gln Lys Glu Pro Lys Asn Lys Thr Phe
            115                 120                 125
Leu Arg Cys Glu Ala Lys Asn Tyr Ser Gly Arg Phe Thr Cys Trp Trp
130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
                180                 185                 190
Cys Gln Glu Asp Ser Ala Cys Pro Ala Ala Glu Glu Ser Leu Pro Ile
                195                 200                 205
Glu Val Met Val Asp Ala Val His Lys Leu Lys Tyr Glu Asn Tyr Thr
                210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
                260                 265                 270
Phe Cys Val Gln Val Gln Gly Lys Ser Lys Arg Glu Lys Lys Asp Arg
                275                 280                 285
Val Phe Thr Asp Lys Thr Ser Ala Thr Val Ile Cys Arg Lys Asn Ala
                290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Gly Ser Gly Gly Gly
                325                 330                 335
Gly Ser Gly Gly Gly Gly Ser Arg Asn Leu Pro Leu Ala Thr Pro Asp
                340                 345                 350
Pro Gly Met Phe Pro Cys Leu His His Ser Gln Asn Leu Leu Arg Ala
                355                 360                 365
Val Ser Asn Met Leu Gln Lys Ala Arg Gln Thr Leu Glu Phe Tyr Pro
                370                 375                 380
Cys Thr Ser Glu Glu Ile Asp His Glu Asp Ile Thr Lys Asp Lys Thr
385                 390                 395                 400
Ser Thr Val Glu Ala Cys Leu Pro Leu Glu Leu Thr Lys Asn Glu Ser
                405                 410                 415
Cys Leu Asn Ser Arg Glu Thr Ser Phe Ile Thr Asn Gly Ser Cys Leu
                420                 425                 430
Ala Ser Arg Lys Thr Ser Phe Met Met Ala Leu Cys Leu Ser Ser Ile
                435                 440                 445
Tyr Glu Asp Ser Lys Met Tyr Gln Val Glu Phe Lys Thr Met Asn Ala
                450                 455                 460
Lys Leu Leu Met Asp Pro Lys Arg Gln Ile Phe Leu Asp Gln Asn Met
465                 470                 475                 480
Leu Ala Val Ile Asp Glu Leu Met Gln Ala Leu Asn Phe Asn Ser Glu
                485                 490                 495
Thr Val Pro Gln Lys Ser Ser Leu Glu Glu Pro Asp Phe Tyr Lys Thr
                500                 505                 510
```

Lys Ile Lys Leu Cys Ile Leu Leu His Ala Phe Arg Ile Arg Ala Val
        515                 520                 525

Thr Ile Asp Arg Val Met Ser Tyr Leu Asn Ala Ser
        530                 535                 540

<210> SEQ ID NO 56
<211> LENGTH: 86
<212> TYPE: PRT
<213> ORGANISM: Artificial Sequence
<220> FEATURE:
<223> OTHER INFORMATION: endodomain derived from human common gamma
      chain

<400> SEQUENCE: 56

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
50                  55                  60

Ala Ser Pro Cys Asn Gln His Ser Pro Tyr Trp Ala Pro Pro Cys Tyr
65                  70                  75                  80

Thr Leu Lys Pro Glu Thr
                85

<210> SEQ ID NO 57
<211> LENGTH: 286
<212> TYPE: PRT
<213> ORGANISM: Artificial Sequence
<220> FEATURE:
<223> OTHER INFORMATION: endodomain derived from human IL-2Rbeta

<400> SEQUENCE: 57

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
50                  55                  60

Arg Asp Lys Val Thr Gln Leu Leu Leu Gln Gln Asp Lys Val Pro Glu
65                  70                  75                  80

Pro Ala Ser Leu Ser Ser Asn His Ser Leu Thr Ser Cys Phe Thr Asn
                85                  90                  95

Gln Gly Tyr Phe Phe Phe His Leu Pro Asp Ala Leu Glu Ile Glu Ala
            100                 105                 110

Cys Gln Val Tyr Phe Thr Tyr Asp Pro Tyr Ser Glu Glu Asp Pro Asp
        115                 120                 125

Glu Gly Val Ala Gly Ala Pro Thr Gly Ser Ser Pro Gln Pro Leu Gln
130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

```
Ser Thr Ala Pro Gly Gly Ser Gly Ala Gly Glu Glu Arg Met Pro Pro
            180                 185                 190

Ser Leu Gln Glu Arg Val Pro Arg Asp Trp Asp Pro Gln Pro Leu Gly
        195                 200                 205

Pro Pro Thr Pro Gly Val Pro Asp Leu Val Asp Phe Gln Pro Pro Pro
    210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
            260                 265                 270

Ser Leu Gln Glu Leu Gln Gly Gln Asp Pro Thr His Leu Val
        275                 280                 285

<210> SEQ ID NO 58
<211> LENGTH: 106
<212> TYPE: PRT
<213> ORGANISM: Artificial Sequence
<220> FEATURE:
<223> OTHER INFORMATION: kappa chain constant domain

<400> SEQUENCE: 58

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 59
<211> LENGTH: 97
<212> TYPE: PRT
<213> ORGANISM: Artificial Sequence
<220> FEATURE:
<223> OTHER INFORMATION: heavy chain constant domain (CH) sequence from
      a gamma immunoglobulin heavy chain

<400> SEQUENCE: 59

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80
```

```
Ile Cys Asn Val Asn His Lys Pro Ser Asn Thr Lys Val Asp Lys Arg
             85                  90                  95
Val
```

NUCLEIC ACID CONSTRUCT

CROSS-REFERENCE TO RELATED APPLICATIONS

This is a U.S. National Phase of International Application No. PCT/GB2019/052150, filed Jul. 31, 2019, which claims priority to Great Britain Application No. 1812474.3, filed Jul. 21, 2018.

FIELD OF THE INVENTION

The present invention relates to constructs and methods for modulating the relative expression of transgenes.

BACKGROUND TO THE INVENTION

Expression of Multiple Transgenes

Gene therapy involves the modification of cells to express biological molecules to treat or correct a pathological condition. Obtaining either a physiological or a therapeutically relevant level of the biological molecule is key to successful gene therapy.

Current methods for modulating gene expression generally rely on modifying promoter regions to either increase or decrease the rate of transcription or to insert regulatory elements in them to render their expression inducible through the action of engineered transcription factors and small molecules.

Gene therapy approaches often involve the expression of more than one transgene. Transduction of a cell with multiple vectors in order to produce multiple products is difficult, expensive and unpredictable. For this reason, various methods have been developed to allow co-expression of two proteins from a single vector (see FIG. 1).

Initial attempts used two different promoters within the same cassette which results in two separate transcripts each of which code for a separate protein. This is a difficult approach for a number of reasons. A key problem is "promoter interference" whereby one promoter dominates and causes silencing of the second promoter. In addition, different promoters work differently in different cellular contexts and this makes consistent "tuning" of the relative expression of each transgene difficult to achieve.

An alternative approach is to use an Internal Ribosome Entry sequence (IRES). Here, a single transcript is generated. The IRES sequence in the transcript is placed between the open reading frames for the two transgenes and mimics an mRNA cap structure. Hence, the ribosome either initiates translation at the 5' cap or the IRES, resulting in expression of two separate proteins. A key limitation with this method is the inability to control relative expression. The 3' transcript is typically expressed less than the 5' one, but the ratio of expression is difficult to predict and tune.

A further approach has been developed following characterization of the role of foot-and-mouth-disease virus (FMDV) 2A peptide in allowing FMDV (and related viruses) to express multiple proteins from a single open reading frame (ORF) (Donnelly et al; J. Gen. Virol.; 82, 1027-1041 (2001)). The 2A peptide (and homologs) cleaves at very high efficiency immediately after translation of the ORF, enabling the expression of multiple peptides from a single ORF. The use of self-cleaving peptides such as the 2A peptide results in expression of the transgenes at a 1:1 ratio.

WO2016/174409 describes the use of altered signal peptides to vary the ratio of transgene expression within a nucleic acid construct. In this system, mutations are introduced into the signal peptide motifs of, for example, type I transmembrane proteins, to reduce the efficacy of trafficking to the cell surface. This approach enables the level of cell surface expression to be reduced approximately 10-fold compared to the wild-type signal peptide motif.

However, this strategy is only suitable to lower the expression of cell-surface proteins, as it works by reducing trafficking of the protein to the cell surface. Moreover, a reduction of expression by 10-fold may not be sufficient for some applications such as the expression of a toxic compound, where overexpression may result in death of the host cell.

There is therefore a need for an alternative approach to alter the relative expression of two or more transgenes in a cell which are not associated with these limitations.

Chimeric Antigen Receptors (CARs)

Chimeric antigen receptor T cell (CAR-T cell) therapy redirects cytolytic T cells to target tumour cells through the expression of a chimeric antigen receptor (CAR) recognising a tumour-specific antigen on their cell surface. A chimeric antigen receptor consists of an antibody or ligand binding motif, a spacer domain and a transmembrane domain, fused to the intracellular signalling domains from the CD3ζ chain of the T cell receptor (TCR). Signalling domains from co-receptors, such as CD28, OX40 or 4-1 BB, may also be included with CD3ζ signalling domain in the CAR 1.

CAR-T cell therapy has demonstrated itself to be an effective treatment for haematological malignancies, such as B cell leukaemia where it has achieved impressive response rates. However, CAR-T cell therapy has failed to achieve the same success in the treatment of solid tumours, where a number of factors compound to limit CAR-T cell activity. These include the expression of immuno-suppressive ligands, such as PD-L1, secretion of cytokines that dampen favourable inflammatory responses, the expression of ligands that induce apoptosis by the tumour cells and nutrient depletion. To overcome the immuno-suppressive tumour microenvironment, CAR-T cells are being engineered to express molecules that block immune-suppressive signalling or enable T cells to survive in the hostile tumour microenvironment.

Cytokines that enhance the inflammatory response can increase the efficacy of CAR-T cell therapy. These include IL-7, IL-12, IL15, IL-17A, IL-18 and IL-21, which have either been shown to enhance the response of CAR-T cells when provided exogenously or be released during CAR T-cell therapy.

IL-12 is a potent immunodulatory cytokine that is normally secreted by phagocytes and dendritic cells in response to: pathogens; T- and natural killer (NK) cell signals; and extracellular matrix components. CAR-T cells have been engineered to express IL-12 either constitutively or from an inducible promoter, and this has been shown to improve the efficacy of CAR-T cell therapy when targeting solid tumours. IL-12 systemically is toxic so CAR T-cells or other immune cells have been engineered to release IL-12 into the tumour microenvironment 1. However, transgenic T-cell IL-12 secretion can result in highly toxic systemic levels.

While the expression of cytokines, chemokines or toxins may improve the efficacy of CAR-T cell therapy, the secretion of these biological molecules must be tightly regulated to limit their toxicity to within safe levels that offer therapeutic benefit and minimal side effects. This could be achieved by regulating the rate of gene transcription from promoter regions by either inserting or deleting cis-acting sequences to obtain the desired level of transcription or introducing inducible elements into promoter region. Notable inducible promoter systems include the tetracycline off and tetracycline off systems, which utilise the tetracycline-responsive element (TRE) in conjunction with an engineered form of the tetracycline repressor protein (TetR), which binds to the 19 bp nucleotide sequence of the TRE 2. In the tetracycline off system, the TetR is fused to the transactivating domain of viron protein 16 (VP16) from herpes simplex virus to generate a tetracycline transactivator (tTA). In the absence of tetracycline, tTA binds to the TRE in the promoter region and potentiates gene transcription; conversely, in the presence of tetracycline, tTA is unable to bind to the TRE and transcription does not occur. Mutation of the TetR domain in tTA to render it dependent on tetracycline for binding to the TRE created a reverse tTA (rtTA) and the tetracycline on system. In the presence of tetracycline the rtTA is able to bind to the TRE and stimulate transcription, but not in its absence. While the tetracycline inducible system enables the control of transgene expression, it relies on the use of a small molecule, the insertion of the TRE into promoter sequences and the expression of either tTA or rtTA to do so, placing a significant burden on the cell.

An alternative approach to controlling gene expression is to use an internal ribosome entry site (IRES). As explained above, an IRES is placed downstream of the primary transgene and facilitates the constitutive expression of an additional transgene, usually at lower levels than the primary transgene. Such an approach has been used to express IL-12 constitutively in CAR-T cells in an attempt to enhance the immune response and circumvent the need for host preconditioning prior to infusion of CAR-T cells. However, the level of expression of IL-12 is unpredictable and still likely to be toxic in vivo.

There is therefore a need for alternative methods for co-expressing a chimeric antigen receptor with a molecule such as a cytokine, chemokine or toxin which is not associated with the disadvantages mentioned above.

CD19 chimera were obtained using the translational readthrough constructs compared to the attenuated signal peptide mutants.

Figure 5:
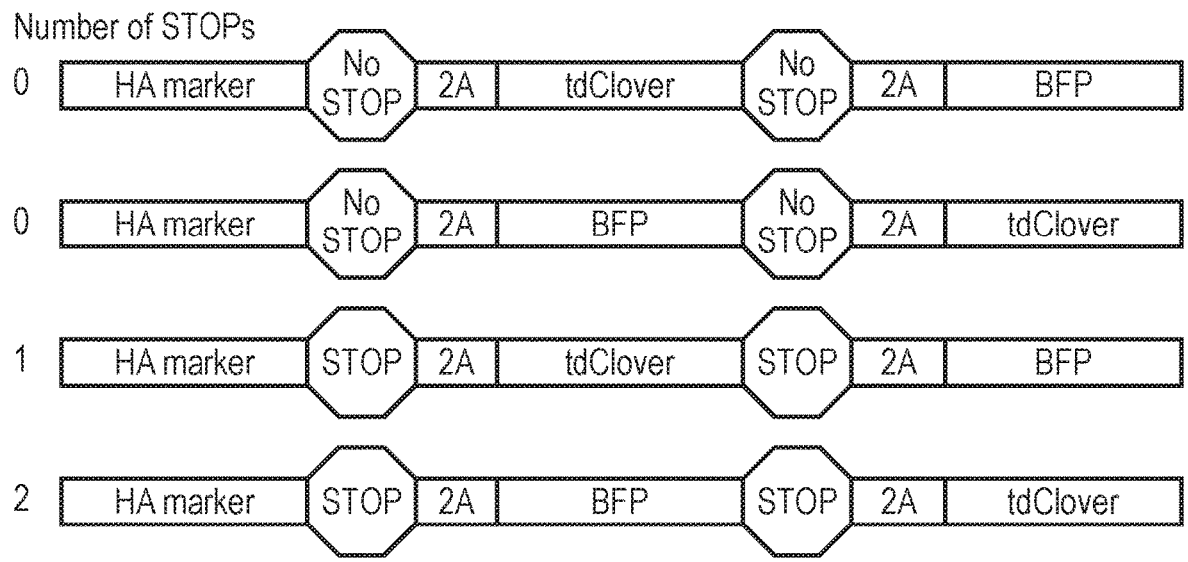
Figure 5:
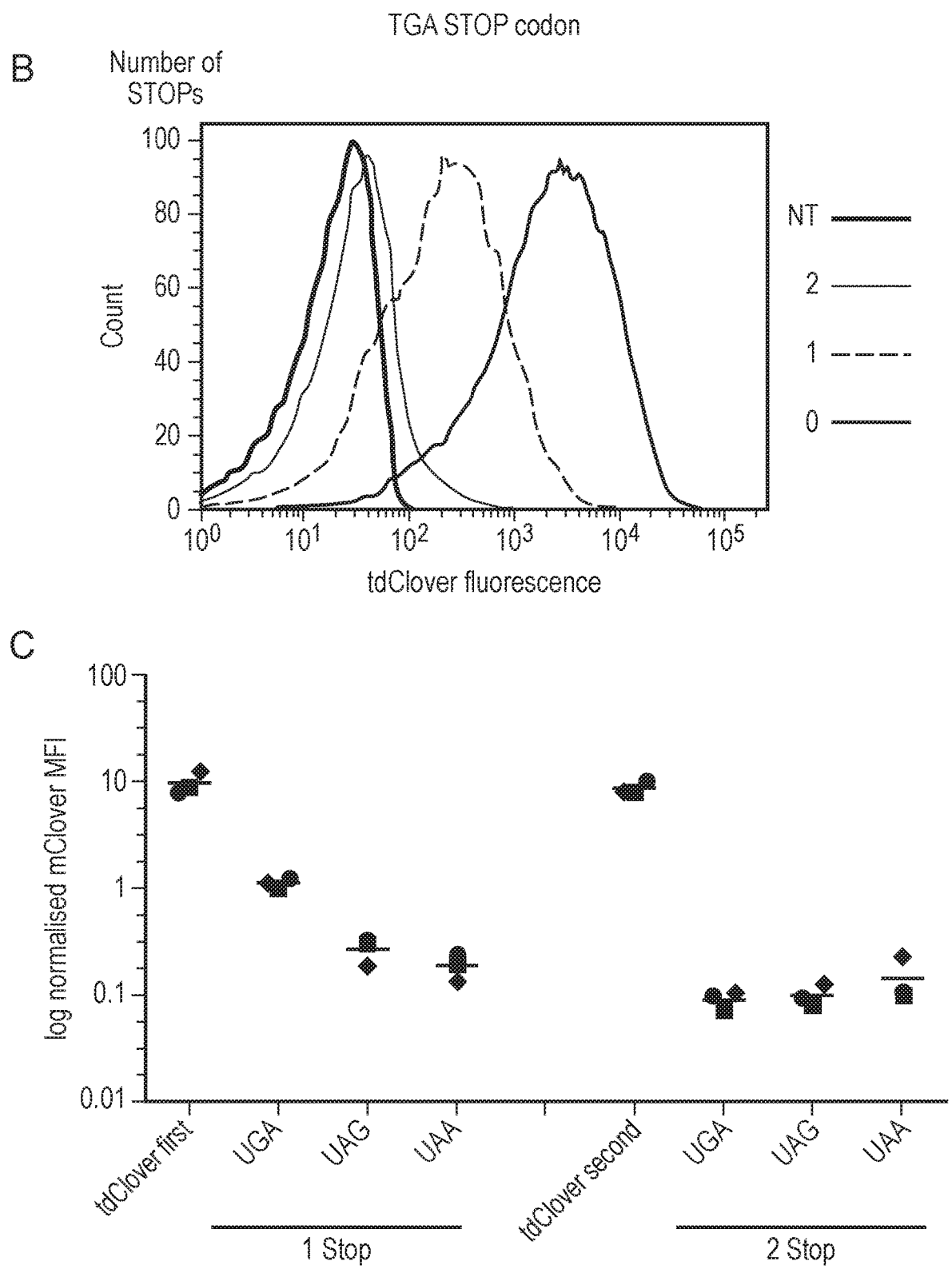

FIG. 5: Translational readthrough motifs in series
A) Diagram of the constructs generated with stop codons and translational readthrough motifs placed in series. For simplicity, only four examples illustrating the structure of the constructs with the translational readthrough motifs in series are shown. The cell surface marker, an HA epitope presented on a CD8a stalk was always at the first position in the cassette, followed by either tandem Clover3 or EBFP with the different coding sequence separated by self-cleaving peptide sequences (2A). Two control constructs were cloned where stop codons were replaced with UGG (encoding tryptophan) and tandem mClover or EBFP were in the second or third position. For the constructs with the translational readthrough motifs in series, all three stop codons were tested (UGA, UAG and UAA) and the translational readthrough motif utilised was CUAG. The same stop codon was used at both positions. B) Flow cytometry of PBMCs transduced with the constructs showing tandem Clover3 fluorescence intensity from constructs with 0, 1 or 2 stop codons/translational readthrough motifs (control is no stop codon with tandem Clover3 in position 2). The histograms show the reduction in tandem Clover3 expression from the constructs possessing the translational readthrough motifs in series, with the levels varying depending on the stop codon present. C) Normalisation of tandem Clover3 fluorescence intensity levels relative to the cell surface marker. When placed immediately downstream of the UGA, UAG or UAA stop codon and the CUAG translational readthrough motif, levels were reduced 6-fold, 24-fold or 33-fold, respectively. When the tandem Clover3 sequence was placed downstream of two stop codons and translational readthrough motifs a 100-fold reduction in tandem Clover3 levels was observed.

Figure 6:
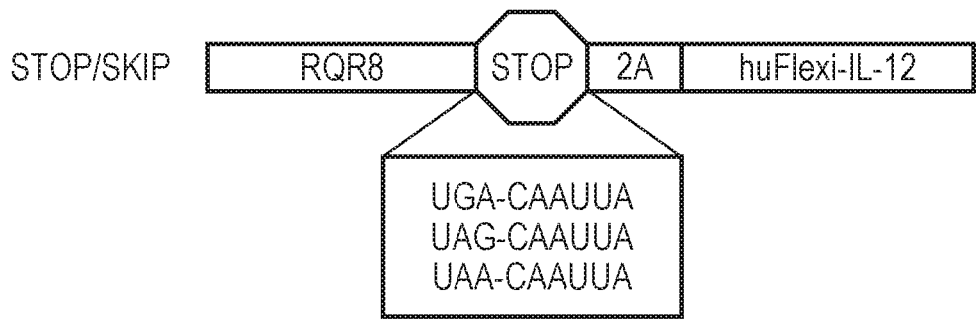
Figure 6:
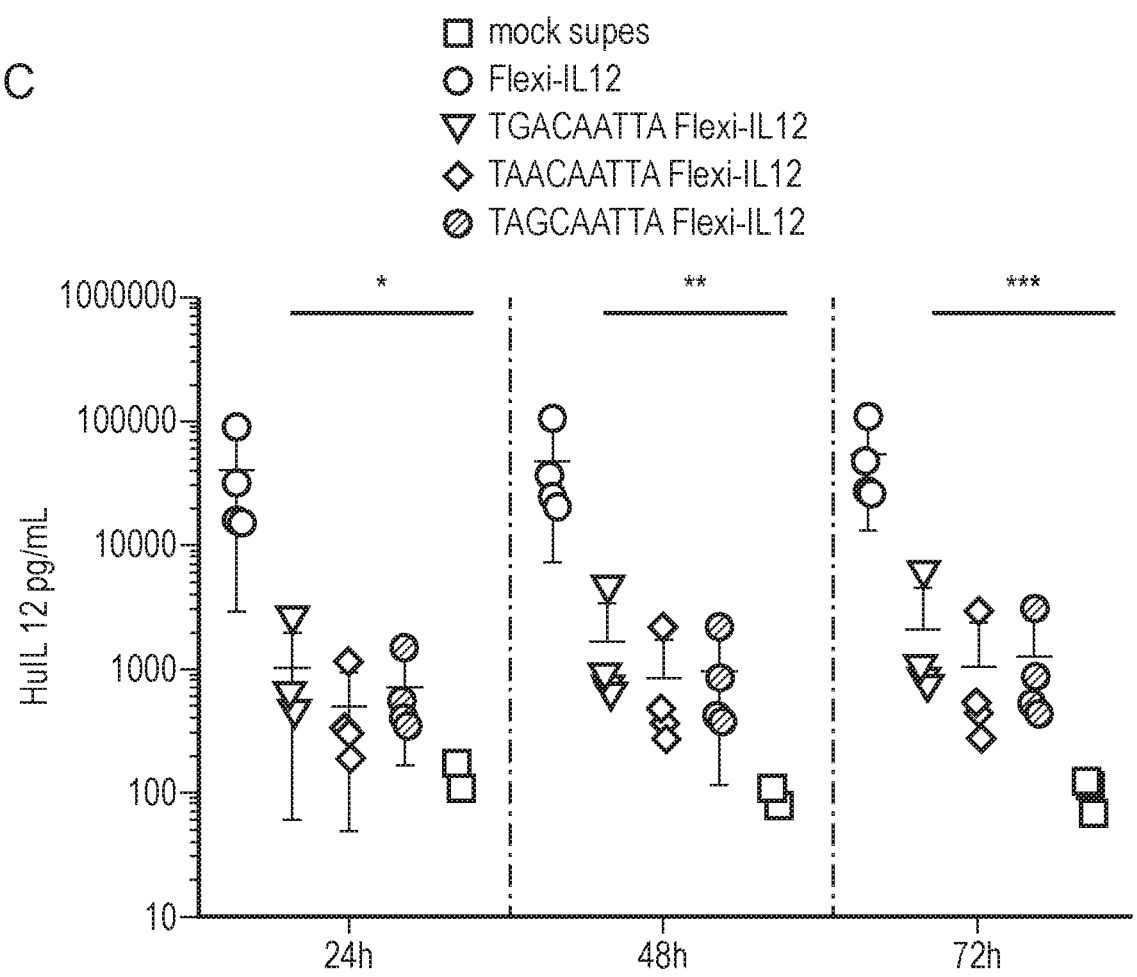
Figure 6:
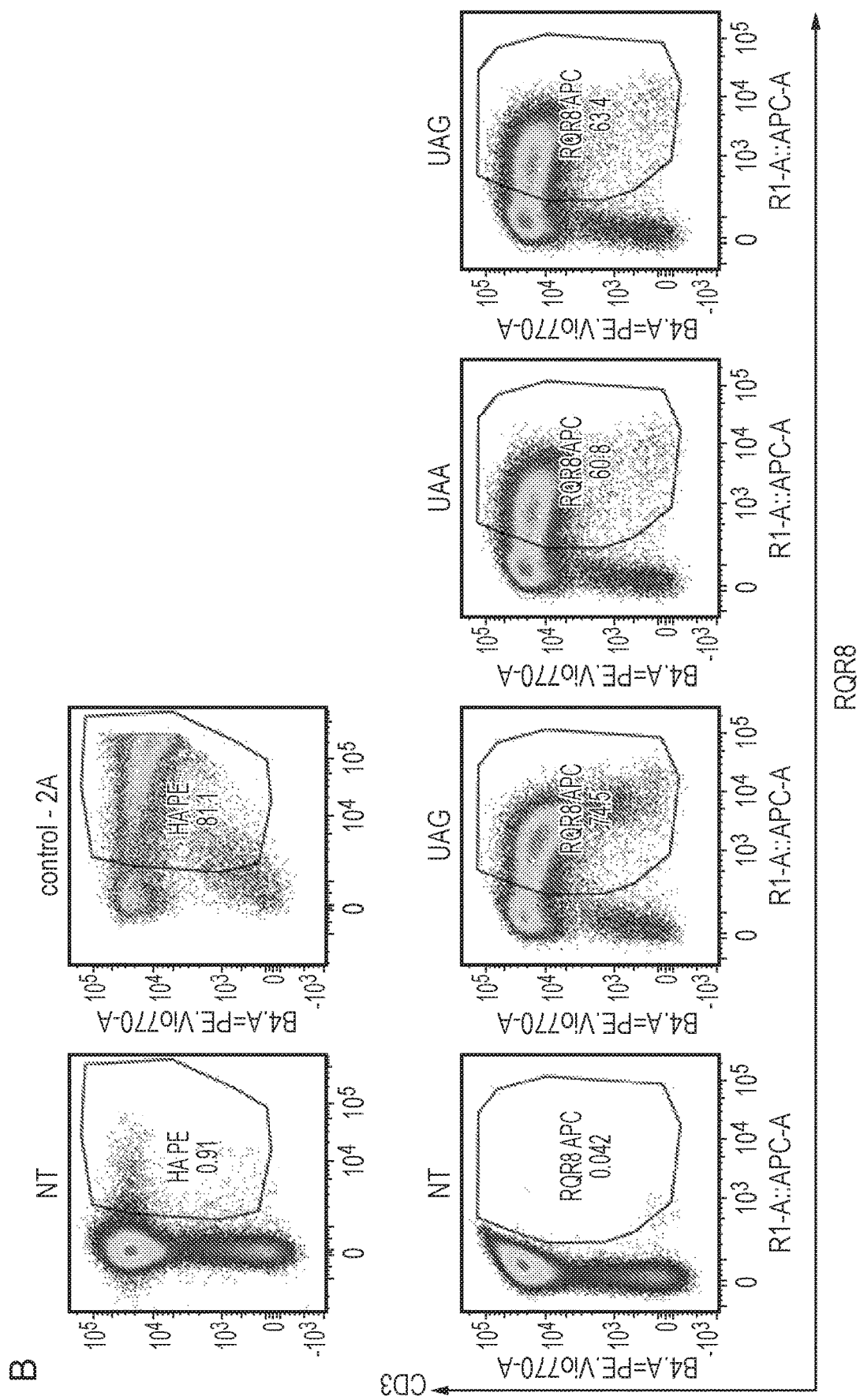

FIG. 6: Controlled expression of human flexi-IL-12 downstream of translational readthrough motifs
A) Diagram showing the structure of the constructs where human flexi-IL-12, consisting of a fusion between the IL-12α (p35) and IL-12β (p40) subunits, was placed downstream of the sort selection marker RQR8 with self-cleaving peptide facilitating expression of both proteins. All three stop codons were tested with the translational readthrough motif CAAUUA. B) Representative flow cytometry plots of PBMCs transduced with the constructs and stained with antibodies to CD3c and RQR8. C) Quantification of secreted IL-12 from transduced PBMCs 24, 48 and 72 hours after determination of the transduction efficiency. The results demonstrate that IL-12 secretion is significantly reduced from the translational readthrough constructs.

Figure 7:
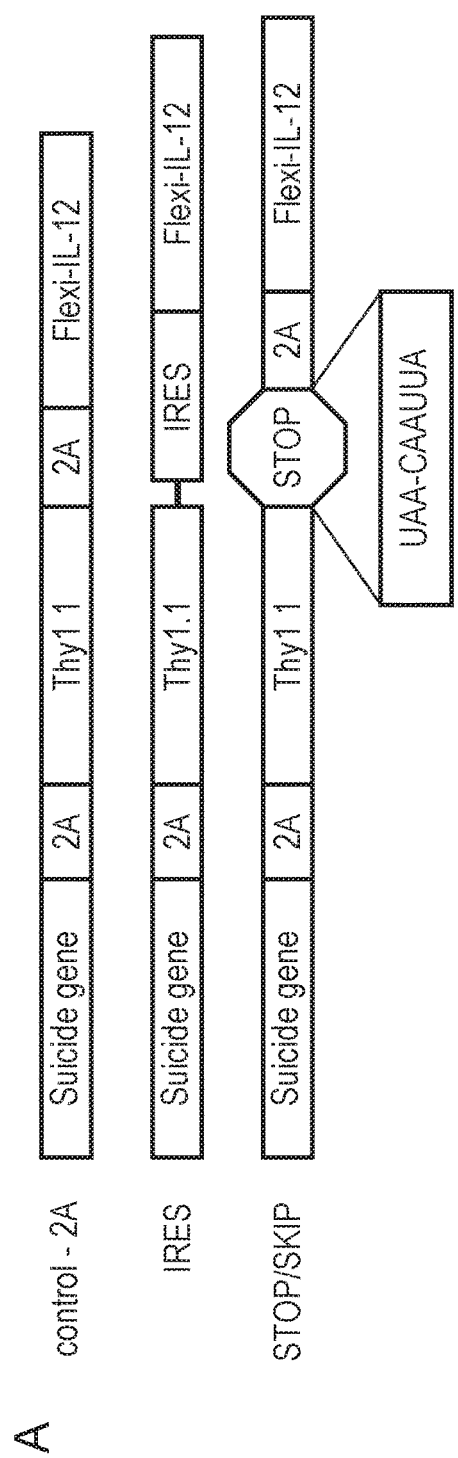
Figure 7:
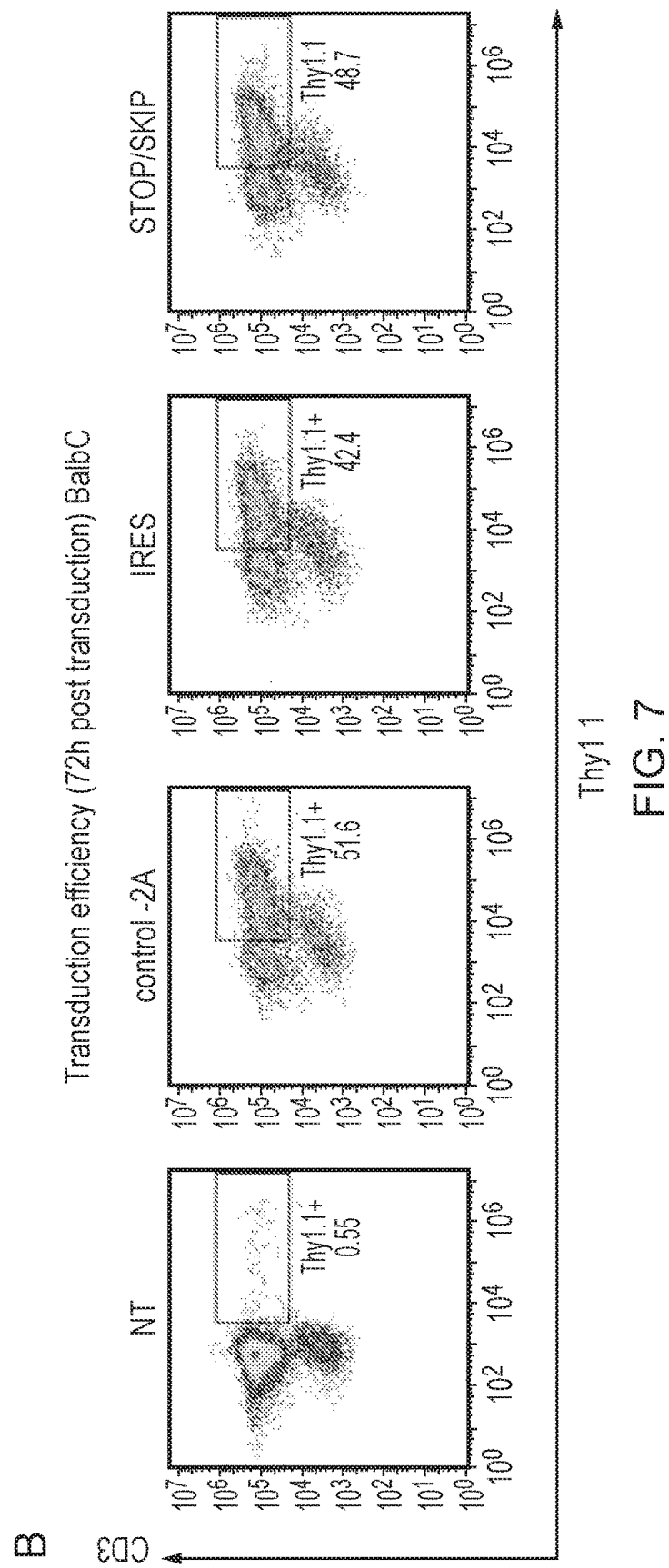
Figure 7:
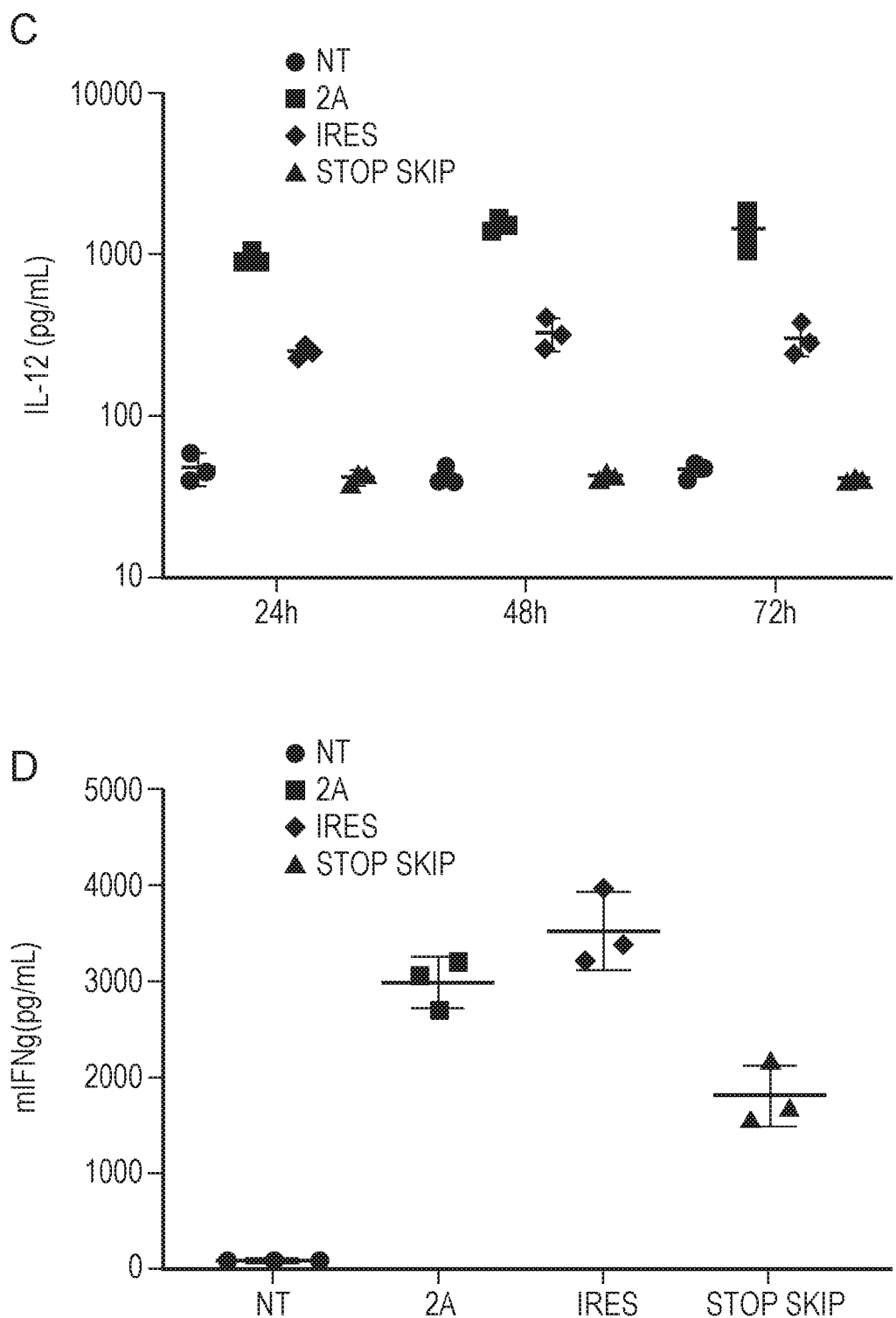

FIG. 7: Controlled expression of murine IL-12 downstream of a translational readthrough motif
A) Diagram of the tri-cistronic constructs with a suicide gene (RapaCasp9), the cell surface marker Thy1.1 and murine flexi-IL-12. Murine flexi-IL-12 levels were modulated by an internal ribosome entry site (IRES), attenuated signal peptide motif or a translational readthrough motif. B) Representative flow cytometry plots of BalbC splenocytes transduced with the constructs and stained with antibodies to CD3 and Thy1.1. C) Quantification of secreted IL-12 levels from the transduced splenocytes by ELISA. D) Supernatant from the transduced splenocytes was used to re-stimulate activated splenocytes. Supernatant from the re-stimulated was analysed for the presence of IFNg by ELISA. Importantly, these results demonstrated that supernatant from the splenocytes transduced with the translational readthrough motif were able to provoke IFNy secretion from the re-stimulated splenocytes.

Figure 8:
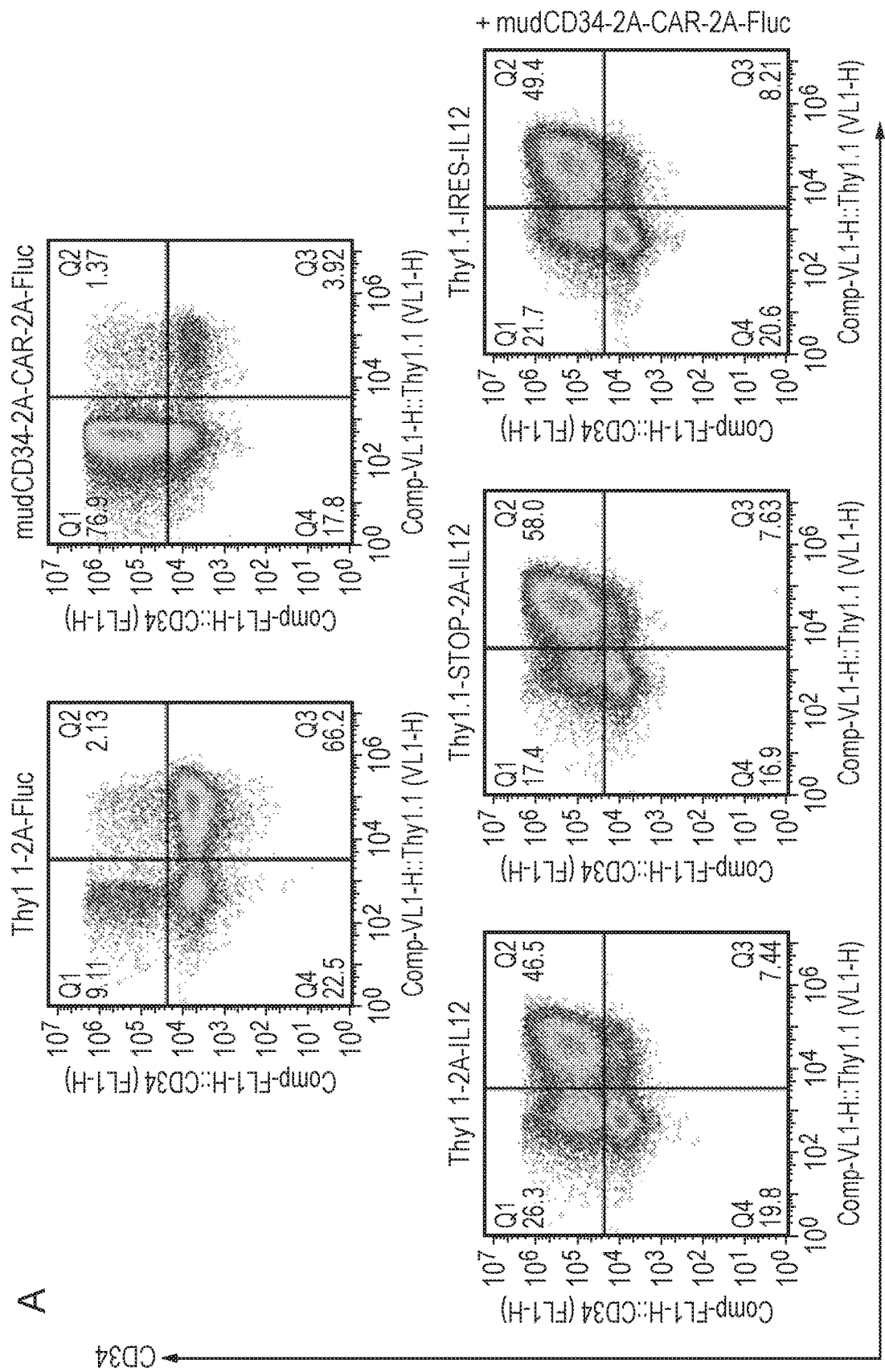
Figure 8:
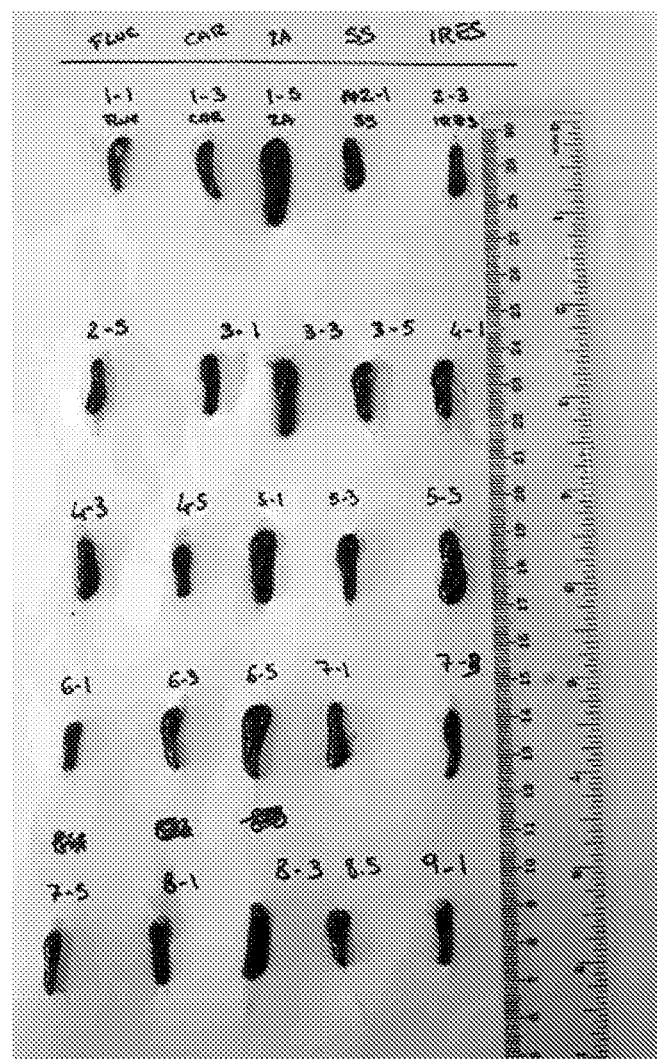

FIG. 8: Toxicity testing of the translational readthrough IL-12 construct
A) Splenocytes were co-transduced with the previously described RapaCasp6, Thy1.1 and IL-12 encoding constructs and a second construct containing truncated murine CD34 (mudCD34), firefly luciferase (FLuc) and an anti-GD2 chimeric antigen receptor (CAR). The transduced splenocytes were stained with antibodies to CD34 and Thy1.1 and flow cytometry carried out to determine transduction efficiency. B) Mice were injected with the transduced splenocytes and after 15 days they were sacrificed and their spleens removed. Splenomegaly was only observed in mice injected with splenocytes transduced with constitutively expressed IL-12 (group marked 2A).

Figure 9:
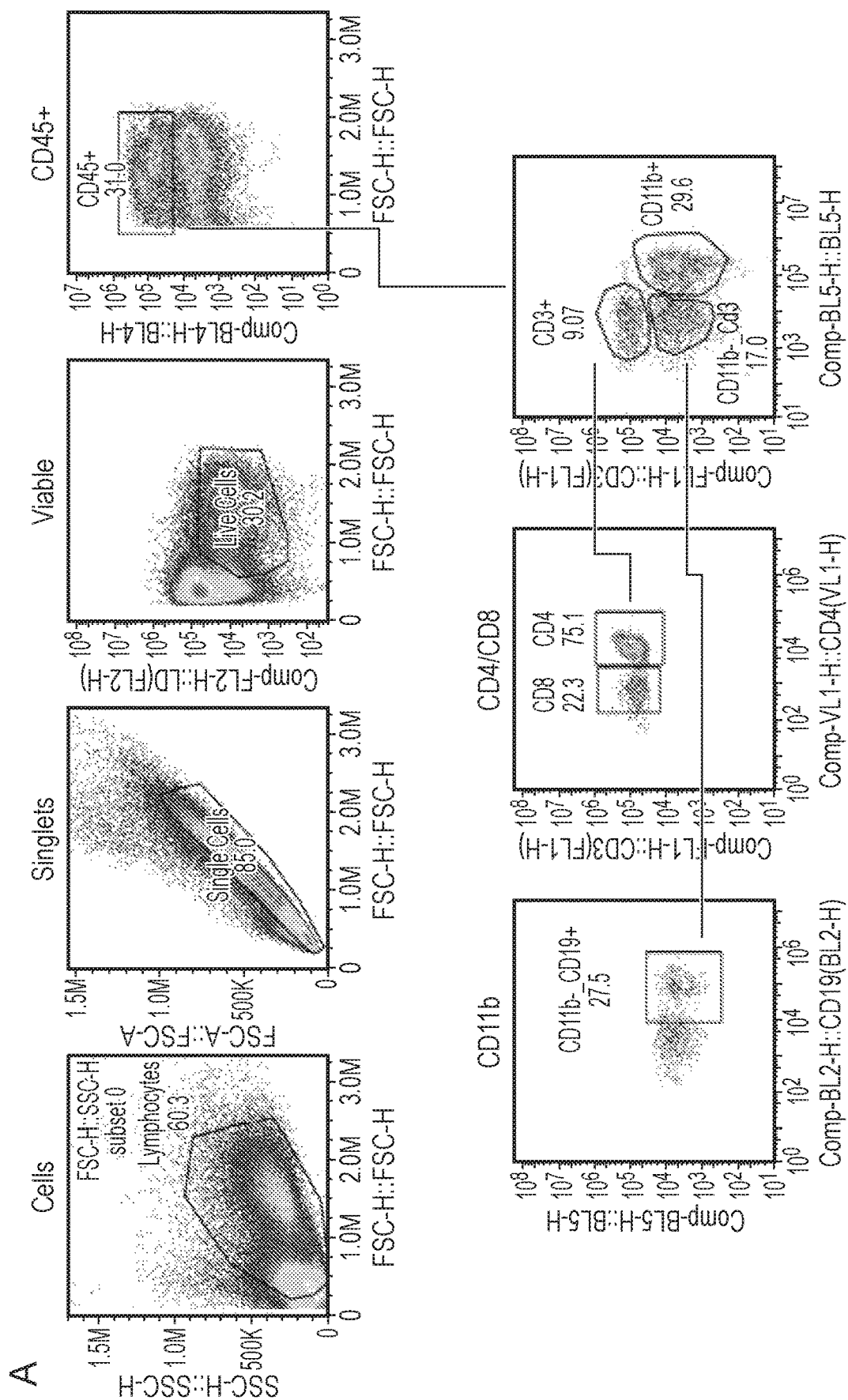
Figure 9:
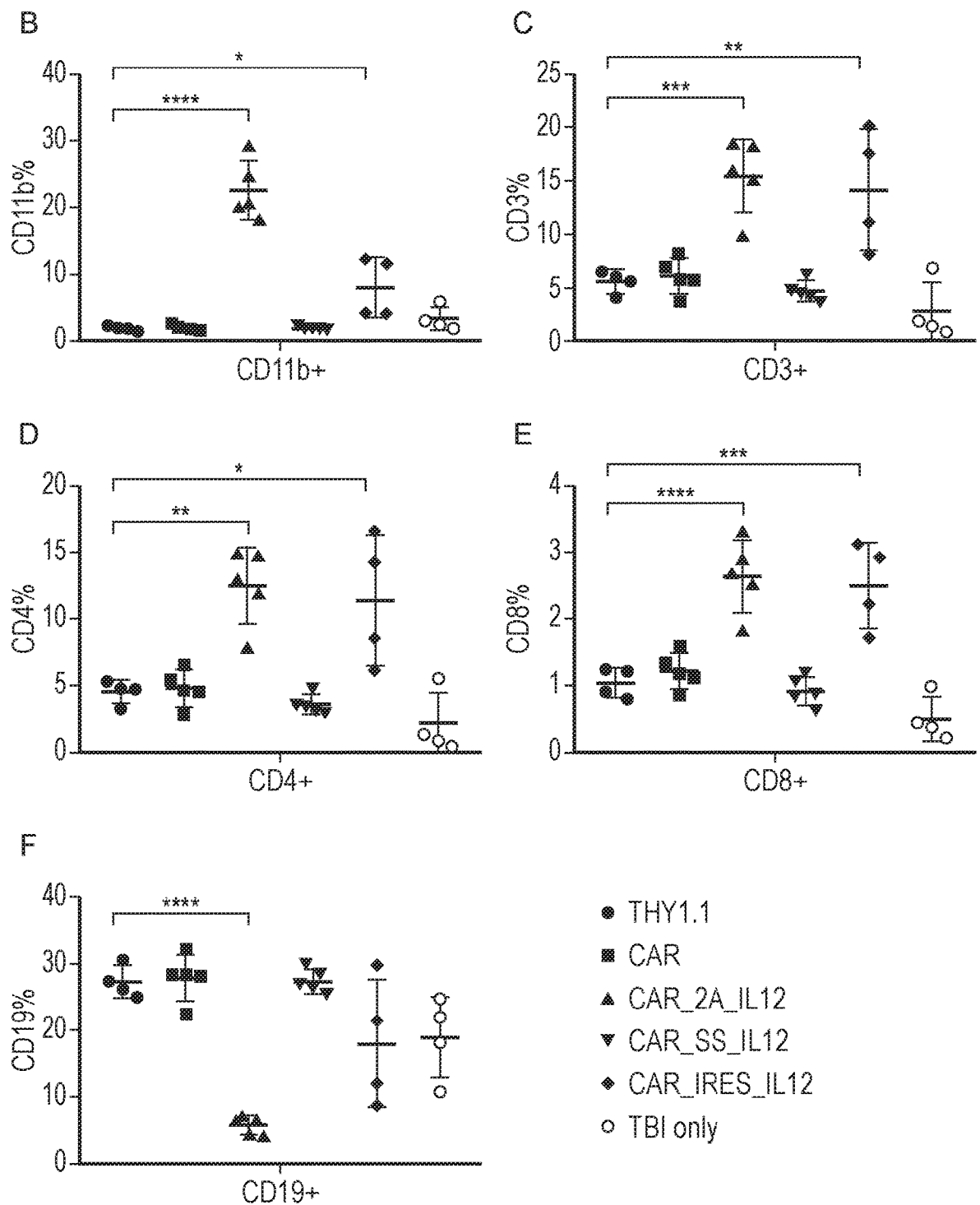

FIG. 9: Flow cytometric analysis of splenocytes
A) Splenocytes from sacrificed mice were stained with antibodies to CD11 b, CD3, CD4, CD8 and CD19 and analysed by flow cytometry. The gating strategy used is shown. B-F) Percentage of CD11 b+(macrophages), CD3+(T cells), CD4+(helper T cells), CD8+(cytotoxic T cells) and C19+(B-cells) present. Increased numbers of macrophages and T cells were present in spleens of mice injected with splenocytes transduced with constructs constitutively expressing IL-12 or from an IRES. A reduction in B-cell numbers was observed in mice with splenocytes constitutively expressing IL-12.

SUMMARY OF ASPECTS OF THE INVENTION

The present inventors have developed a system which uses frame-slip or translational readthrough as a means of regulating the expression of a transgene. In particular, the system can be used to control the relative expression of two or more transgenes expressed from a single mRNA transcript.

Thus, in a first aspect, the present invention provides a nucleic acid construct comprising: a first nucleotide sequence of interest (NOI1); a frame-slip motif or a translational readthrough motif (FSM/TRM); and a second nucleotide sequence of interest (NOI2).

The nucleic acid construct may also comprises a nucleotide sequence encoding a cleavage site (CL), so that NOI1 and NOI2 are expressed as separate proteins.

The nucleic acid construct may comprise the structure:
NOI1-FSM/TRM-CL-NOI2 or NOI1-CL-FSM/TRM-NOI2.

In particular the nucleic acid construct comprise the structure:
NOI1-CL-FSM-NOI2; or
NOI1-TRM-CL-NOI2.

The nucleic acid construct may comprise more than two nucleotide sequences of interest. For example, the nucleic acid construct may have the structure:
NOI1-FSM1/TRM1-CL1-NOI2-FSM2/TRM2-CL2-NOI3, or
NOI1-CL1-FSM1/TRM1-NOI2-CL2-FSM2/TRM2-NOI3
in which:
NOI1, NOI2 and NOI3 are nucleotide sequences of interest;
FSM1/TRM1 and FSM2/TRM2, which may be the same or different, are frame-slip motifs or translational readthrough motifs; and
CL1 and CL2, which may be the same or different, are nucleic acid sequences each encoding a cleavage site.

A frame-slip motif (FSM) may comprise a repeat of uracil, thymine or guanine bases, such as the sequence UUUUUUU (SEQ ID No. 1).

A frame-slip motif may also comprise a stop codon. For example, a FSM may comprise one of the following sequences:

UUUUUUUGA (SEQ ID NO. 2)

UUUUUUUAG (SEQ ID NO. 3)

UUUUUUUAA. (SEQ ID NO. 4)

A translational readthrough motif (TRM) may comprise the sequence STOP-CUAG or STOP-CAAUUA, in which "STOP" is a stop codon. For example, a translational readthrough motif may comprise one of the following sequences:

UGA-CUAG (SEQ ID No. 5)

UAG-CUAG (SEQ ID No. 6)

UAA-CUAG (SEQ ID No. 7)

UGA-CAAUUA (SEQ ID No. 8)

UAG-CAAUUA (SEQ ID No. 9)

UAA-CAAUUA (SEQ ID No. 10)

A nucleic acid construct comprising a translational readthrough motif may comprise two adjacent TRMs which may be the same or different.

A nucleic acid construct comprising a translational readthrough motif may comprise two nucleic acid sequences, each encoding a cleavage site. The TRM may be positioned between the two cleavage site-encoding sequences, or there may be two TRMs, each positioned upstream of a cleavage site.

A nucleic acid construct comprising a translational readthrough motif may comprise an attenuated or inefficient signal peptide, positioned upstream of the second (or subsequent) nucleotide of interest.

A nucleic acid construct comprising a translational readthrough motif may have one of the following structures:
NOI1-TRM-CL-NOI2
NOI1-TRM1-TRM2-CL-NOI2
NOI1-CL1-TRM-CL2-NOI2
NOI1-TRM-CL-SP-NOI2
NOI1-TRM1-CL1-NOI2-TRM2-CL2-NOI3
NOI1-TRM1-CL1-TRM2-CL2-NOI2
in which:
TRM1 and TRM2, which may be the same or different, are first and second translational readthrough motifs;
CL1 and CL2, which may be the same or different, are first and second nucleic acid sequences each encoding a cleavage site
SP is an attenuated signal peptide; and
NOI3 is a third nucleotide sequence of interest.

The cleavage site may, for example, comprise a self-cleaving peptide, a furin cleavage site or a Tobacco Etch Virus cleavage site.

The cleavage site may, for example, comprise a 2A self-cleaving peptide from an aphtho- or a cardiovirus or a 2A-like peptide.

The second (or subsequent) nucleotide of interest may encode a cytokine, chemokine or toxin.

The nucleic acid construct may be capable of producing two products when expressed in a cell:
a) a first product encoded by NOI1 alone; and
b) a second product, encoded by NOI1 and NOI2, which is produced when frame-slip or translational readthrough occurs.

In this embodiment, the second product may be a chimeric antigen receptor (CAR) and the first product may be a truncated version of the CAR, incapable of inducing CAR-mediated cell signalling.

Alternatively, the first product may be a chimeric antigen receptor (CAR) comprising an intracellular signalling domain (i.e. a first generation CAR) and the second product is a CAR comprising an intracellular signalling domain and one or more co-stimulatory domain(s) (i.e. a second or third generation CAR.

In a second aspect, the present invention provides a vector comprising a nucleic acid construct according to the first aspect of the invention.

The vector may, for example, be a retroviral vector or a lentiviral vector.

In a third aspect, the present invention provides a cell comprising a nucleic acid construct according to the first aspect of the invention or a vector according to the second aspect of the invention.

In a fourth aspect, the present invention provides a method for making a cell according to the third aspect of the invention which comprises the step of introducing a nucleic acid construct according to the first aspect of the invention or a vector according to the second aspect of the invention into a cell.

In a fifth aspect, there is provided a method for modulating the relative expression of two transgenes in a nucleic acid construct, which comprises the step of including a frame-slip motif or a translational readthrough motif between the two transgenes in order to reduce the expression of the downstream transgene.

A significant advantage of using frame-slip or translational readthrough as a means of controlling transgene expression is that a broad range of expression is achievable and, where two transgenes are expressed, the level of expression of the second transgene can be reduced to less than 1% of the first transgene. This is considerably lower than the levels that can be achieved using altered signal peptides and enables the technology to be used for the expression of proteins such as toxic compounds, where a very low level of expression is essential.

The use of frame-slip or translational readthrough enables the expression of transgenes at predictable and defined ratios. It is also possible to tune the level of transgene expression by using different frame-slipping or readthrough motifs.

The system can be used to control the expression of any transgene and is not limited to the expression of cell-surface proteins.

DETAILED DESCRIPTION

The present invention relates to a nucleic acid construct comprising a motif which reduces the expression of a transgene, such as a frame-slip motif or a translational readthrough motif.

Frame-Slip

During transcription, RNA polymerase catalyzes incorporation of nucleotides into growing RNA chains on the basis of complementarity to the DNA template. When RNA polymerase encounters a stretch of repeated bases, however, slippage or 'stuttering' can occur. Transcription slippage is utilized in nature, for example for regulation of the *Escherichia coli* pyrBI and codBA operons, expression of the P gene in paramyxoviruses and decoding of the cellular dnaX gene of *Thermus thermophiles*.

When RNA polymerase slips this can result in the synthesis of an mRNA encoding an alternative reading frame because it lacks one (or maybe two) of the repeated bases.

The nucleic acid construct of the present invention may comprise a transcriptional frameslip site, such that transcription of the downstream transgene only occurs if these is slippage of the RNA polymerase resulting in mRNA encoding an alternative reading frame.

Translation of an mRNA sequence to protein is a complex process involving the orchestration of ribosomes, initiation and elongation factors, aminoacyl transfer RNAs (aa-tRNAs), aminoacyl tRNA synthetases and release factor. The initiation of translation begins when a complex of factors binds to the 5' end of the mRNA, which then results in the recruitment of 40S ribosomes and the scanning of the mRNA. When the complex of initiation factors and 40S ribosomes encounters a codon (a triplet of nucleotides) encoding the amino acid methionine (AUG codon), the 60S ribosome is recruited and polypeptide synthesis begins with the pairing of cognate tRNAs loaded with the appropriate amino acid. Initiation of translation can occur at alternative start codons other than AUG, but it is the most frequently used start codon. Extension of the polypeptide occurs in a cyclical manner, whereby a tRNA binds to its cognate codon, a peptide bond forms between the newly added amino acid and the extending polypeptide, and the polypeptide translocates to expose the next codon.

During translation, ribosome pausing may occur where the ribosome arrests at a particular codon. Ribosome pausing can promote mRNA degradation by a nucleocytic pathway or it can induce a slip in the −1 or −2 direction. Repetitive sequences within an mRNA, such as UUUUUUA, are known to induce translational frameslipping, and this sequence is present at the 3' end of the group-specific antigen gene (gag) and polymerase (pol) gene of the human immunodeficiency virus (HIV). Translational frameslipping −1 of the HIV gag/pol gene results in the expression of the Gag-Pol polyprotein.

The nucleic acid construct of the present invention may comprise a translational frameslipping site, such that translation of the downstream transcript only occurs if these is a frameslip by the ribosome.

The frame-slip site may comprise a stretch of bases of the same type.

The frame-slip motif may be placed upstream and/or downstream of a cleavage site in the nucleic acid construct. The frame-slip motif is located between first and second transgenes in the nucleic acid construct.

The frame-slip motif may be used alone. In this embodiment, the second transgene may be placed out of frame downstream of the frame-slipping site, such that frame-slip is needed for transcription or translation of the second transgene.

The motif may, for example comprise a stretch of 5, 7, 8, 10 or 11 bases. The site may, for example, comprise a repeat of uracil, adenosine or guanine bases. The site may, for example, comprise the sequence shown as SEQ ID No. 1

UUUUUUU. (SEQ ID No. 1)

Alternatively, the frame-slip site may be used in combination with a stop codon. In this embodiment, a stop codon is positioned in frame downstream of the frame-slip site, such that frame-slipping is required for the stop codon to be ignored.

The stop codon may be UGA, UAG or UAA. The frame-slip site may comprise a repeat of uracil, adenosine or guanine bases in multiples of three, for example, 3, 6 or 9 repeats of uracil, adenosine or guanine bases.

Examples of frame-slip site/stop codon combinations are shown as SEQ ID No. 2, 3 and 4.

UUUUUUUGA (SEQ ID NO. 2)

UUUUUUUAG (SEQ ID NO. 3)

UUUUUUUAA. (SEQ ID NO. 4)

Translational Readthrough

Translation terminates when the ribosome encounters a UGA, UAG or UAA stop codon. At this point, release factor recognises the stop codon and facilitates dissociation and recycling of the ribosome. Termination of translation usually occurs with high fidelity, with recoding of the stop codon, due to competition between release factor and a near cognate tRNA, and continued extension of the polypeptide only occurring 0.1% of the time. However, an elevated level of stop codon of recoding, which results in translational readthrough, has been reported in certain genes. In some cases, this has resulted in the generation of a longer polypeptide with additional functional motifs, in a process referred to as functional readthrough.

Translational readthrough occurs when release factor 1 (RF1) fails to recognise a stop codon and a near cognate aa-tRNA inserts an amino acid into the extending polypeptide, thereby suppressing the stop codon. The local concentration of release factor and the aa-tRNAs affects the level of stop codon suppression and translational readthrough, with low concentrations of release factor promoting translational readthrough. In mammals suppression of the UAG stop codon results in the insertion of a tryptophan, arginine or cysteine residue.

One of the earliest discovered examples of stop codon suppression is the rabbit beta globin gene, where translational readthrough results in the addition of 22 amino acids to the C-terminus of the protein 3.

The frequency of translational readthrough depends on a number of factors including: 1) the stop codon used (UGA, UAG or UAA); 2) the immediate sequence flanking the stop codon, with the six nucleotides upstream and downstream of the stop codon being particularly important and; 3) the presence of cis-acting sequences in the 3' end of the mRNA.

The termination efficiency of the three stop codons varies, with UAA being the strongest stop codon and UGA being the weakest and hierarchy of termination efficiency is defined as UAA>UAG>UGA. Consequently, the highest level of translational readthrough is exhibited with the UGA stop codon and the lowest with the UAA stop codon.

Sequence analysis of genes exhibiting translational readthrough has identified at least two different motifs that promote stop codon suppression and sustained translation:

STOP-CUAG and STOP-CAAUUA (where stop can be UGA, UAG or UAA). The level of translational readthrough is dependent on the stop codon used: UGA supports the highest level of translational readthrough and decreasing levels of readthrough are obtained from the UAG and UAA stop codons, so the overall hierarchy of readthrough is UGA>UAG>UAA.

The nucleic acid construct of the present invention may comprise one of the sequences shown as SEQ ID No. 5 to 10.

UGACUAG (SEQ ID No. 5)

UAGCUAG (SEQ ID No. 6)

UAACUAG (SEQ ID No. 7)

UGACAAUUA (SEQ ID No. 8)

UAGCAAUUA (SEQ ID No. 9)

UAACAAUUA (SEQ ID No. 10)

The translational readthrough site may be located between first and second transgenes in the nucleic acid construct. The translational readthrough site may be placed upstream and/or downstream of a cleavage site in the nucleic acid construct. The translational readthrough site may be flanked by cleavage sites (FIG. 3C). Two or more translational readthrough site may be used, for example, either positioned next to each other (FIG. 3B'), or flanking a cleavage site (Figure E').

Figure 1:
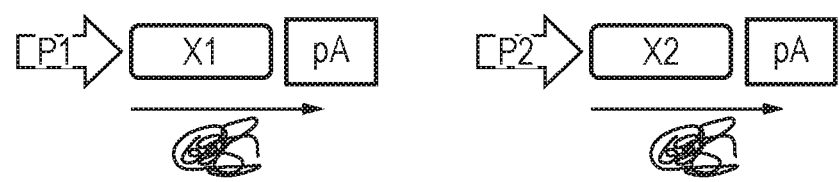
FIG. 1: Methods utilised to express different proteins from the same vector
(a) Two different promoters within the same cassette result in two different transcripts which each give rise to separate proteins. (b) Use of an Internal Ribosome Entry sequence (IRES) leads to a single transcript which is translated into two separate proteins. (c) Use of the FMDV 2A peptide results in a single transcript, and a single polyprotein which rapidly cleaves into two separate proteins.
Figure 1:
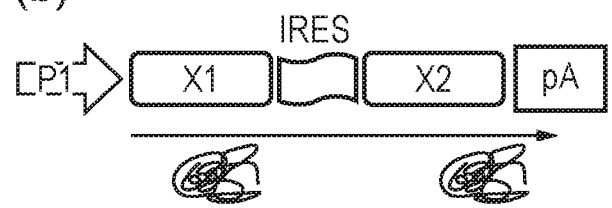
Figure 1:
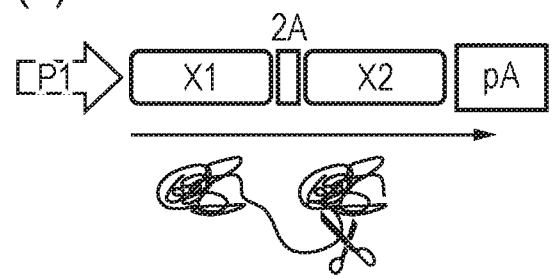
Figure 2:
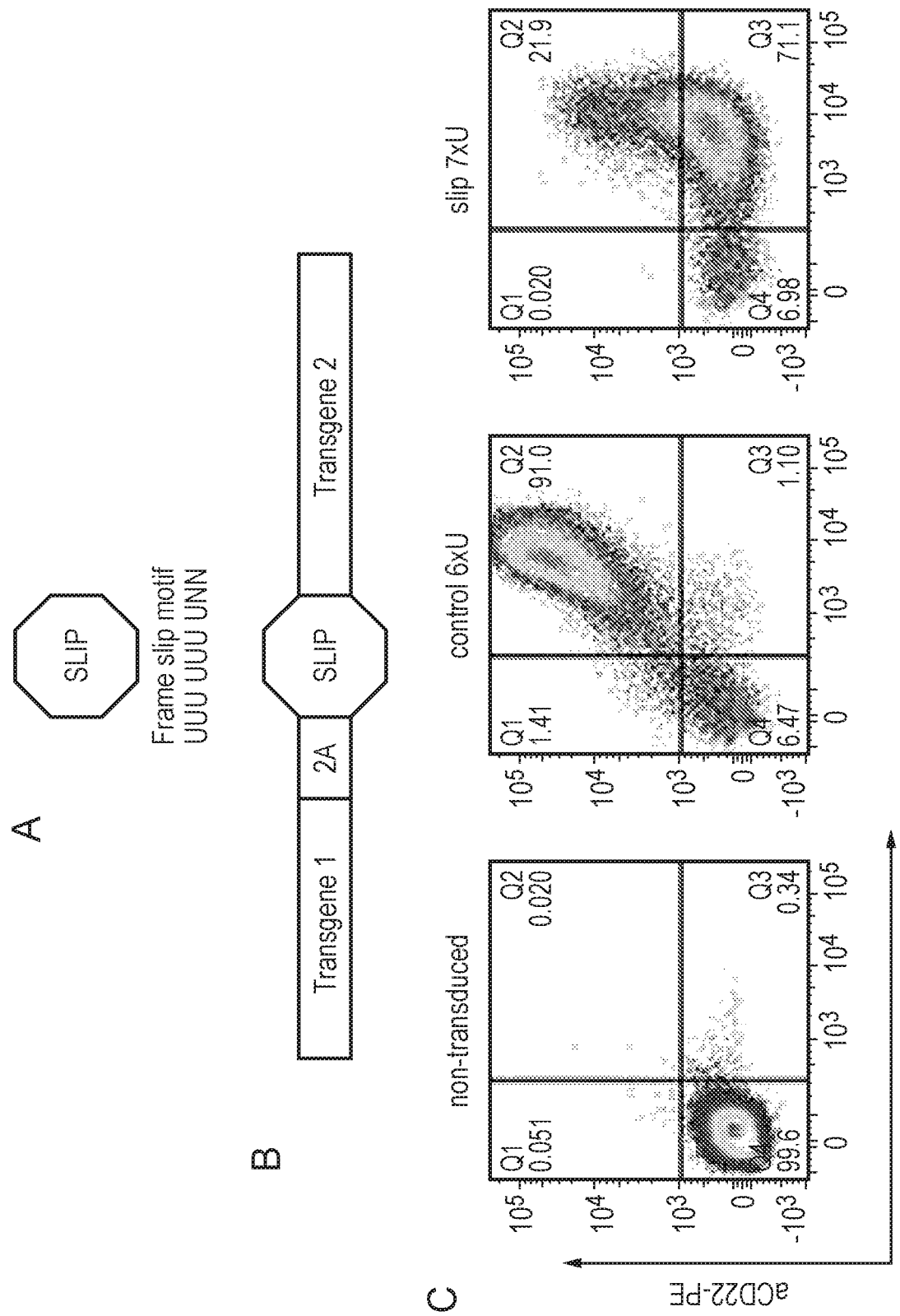
FIG. 2: Frame slip motifs and construct design
(A) Diagram illustrating a frame-slip motif where a series of seven uridines are inserted into the transgene sequence, which promotes frame-slip. Frameslipping results in continued transcription/translation of an alternative reading frame, usually in the −1 direction, and the generation of a functional protein. (B) Structure of a construct showing the locations of the transgenes, the frameslip motif (SLIP) and the 2A self-cleaving peptide sequence. (C) Flow cytometric analysis SupT1 cells transduced with constructs containing the RQR8 sort-selection marker followed by either a control sequence (6xU) or a frameslip motif (7xU) and a CD22-CD19 chimeric protein consisting of the ectodomain of CD22 fused to the transmembrane and truncated endodomain of CD19. Introduction of the frameslip motif resulted in dramatically reduced expression of the CD22-CD19 chimera while similar levels of the RQR8 sort selection marker were observed.

To reduce the expression level of a downstream transgene further, multiple stop codons can inserted 5' of the translational readthrough motif (FIG. 2B). An example multiple stop translational readthrough motif is shown as SEQ ID NO. 11, where two UGA stop codons are positioned 5' of the CUAG readthrough motif.

UGAUGACUAG. (SEQ ID No. 11)

Where a nucleic acid construct comprises more than two transgenes, compound translational readthrough motifs may be placed in series, 5' for sequences encoding cleavage sites. This enables multiple transgenes to be expressed at different ratios. With each additional readthrough motif the level of expression should be reduced 10 to 50-fold relative to the upstream transgene.

A nucleic acid construct with compound translational readthrough motifs may have the structure:

NOI1-TRM1-CL1-NOI2-TRM2-CL2-NOI3

Figure 3:
FIG. 3: Translational readthrough motifs and construct design.
(A) Examples of known translational readthrough motifs. (B-F) Structure of translational readthrough motif constructs. (B) Translational readthrough construct consisting of two transgenes where the translational readthrough motif is placed 3' of the first transgene and 5' of 2A self-cleaving peptide sequence and transgene 2. Expression of transgene 1 will be significantly higher than transgene 2. (B') Double stop translational readthrough construct where two stop codons are incorporated into the translational readthrough motif to reduce expression levels even further than those achieved with a single stop codon. (C) Universal translational readthrough construct consisting of a translational readthrough motif flanked by two 2A self-cleaving peptide sequences. This construct mitigates sequence-dependent effects that can result in unpredictable levels of translational readthrough. (D) Combinatorial approach where a translational readthrough motif is combined with an attenuated signal peptide sequence to reduce the level of expression of transgene 2 even further. (E and E') Compound translational readthrough motifs where multiple motifs are placed in series to produce a cascade of reduced transgene expression. (E) Multiple transgene are expressed from a single cassette using translational readthrough motifs and 2A self-cleaving peptide sequences. (E') Self-cleaving peptide sequences are used to separate the translational readthrough motifs, which are 5' of transgene 2. (F and F') Functional translational readthrough constructs. (F) Secretion of an antigen-binding domain (scFv/VHH) and a functional CAR can be achieved by placing a translational readthrough motif 3' of the spacer domain of the CAR. Functional readthrough results in the expression of a functional CAR, while termination of translation at the stop codon produces secreted antibody. (F') Combinations of first, second and third generation CARs can be produced by placing a translational readthrough motif 3' of the first endodomain (either a CD3 endodomain or a co-receptor endodomain). Functional translational readthrough will switch expression from a first generation CAR to a second or third generation CAR.
Figure 3:
Figure 3:
Figure 3:
Figure 3:
Figure 3:
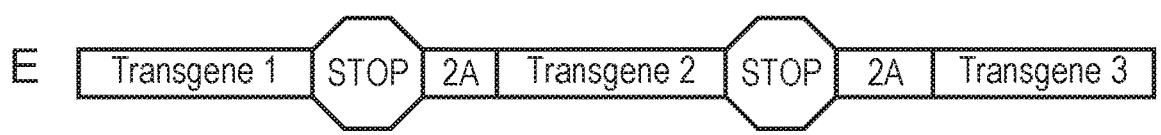
Figure 3:
Figure 3:
Figure 3:
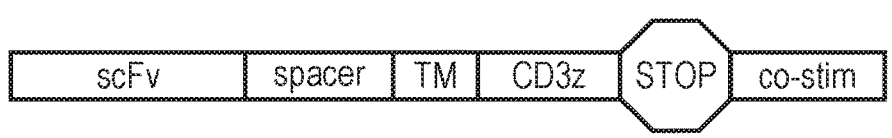

The readthrough site may be positioned within a coding sequence, so that two versions of a protein are made: a short version, made by translation of the transcript up to the readthrough site (i.e. where no readthrough occurs) and a long version, made by translation of the transcript beyond and downstream of the readthrough site (where readthrough occurs). Examples of such arrangements are shown in FIGS. 3, F and F'.

Altered Signal Peptides

While translational readthrough motifs significantly decrease transgene expression, in certain situations it might be necessary to reduce the expression levels even further. For type I transmembrane and secreted proteins a further reduction in expression can be achieved by combining a translational readthrough motif with an altered signal peptide sequence. Such an approach is amenable to type I transmembrane proteins, which have a signal peptide sequence, and secreted proteins. In this case, the altered signal peptide and second transgene are placed 3' of the translational readthrough motif and self-cleaving peptide sequence (FIG. 3D).

A signal peptide is a short peptide, commonly 5-30 amino acids long, present at the N-terminus of the majority of newly synthesized proteins that are destined towards the secretory pathway. These proteins include those that reside either inside certain organelles (for example, the endoplasmic reticulum, golgi or endosomes), are secreted from the cell, and transmembrane proteins.

Signal peptides commonly contain a core sequence which is a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide is commonly positioned at the amino terminus of the molecule, although some carboxy-terminal signal peptides are known.

Altered signal peptides are described in detail in WO2016/174409, which is herein incorporated by reference. The altered signal peptide may comprise one or more mutation(s), such as substitutions or deletions, such that it has fewer hydrophobic amino acids than the wild-type signal peptide from which it is derived. The term "wild type" means the sequence of the signal peptide which occurs in the natural protein from which it is derived.

Where the nucleic acid construct comprises two transgenes both encoding transmembrane proteins, the protein encoded by the downstream transgene (which has lower relative expression) may comprise fewer hydrophobic amino acids than the protein encoded by the upstream transgene (which has higher relative expression).

The hydrophobic amino acids mutated in order to alter signal peptide efficiency may be: Alanine (A); Valine (V); Isoleucine (I); Leucine (L); Methionine (M); Phenylalanine (P); Tyrosine (Y); or Tryptophan (W).

The altered signal peptide may comprise 1, 2, 3, 4 or 5 amino acid deletions or substitutions of hydrophobic amino acids. Hydrophobic amino acids may be replaced with non-hydrophobic amino acids, such as hydrophilic or neutral amino acids.

Nucleic Acid Construct

The present invention relates to a nucleic acid construct comprising: a first nucleotide sequence of interest (NOI1); a frame-slip motif or a translational readthrough motif (FSM/TRM); and a second nucleotide sequence of interest (NOI2).

A "nucleotide of interest" may be RNA or DNA. A nucleotide of interest (N01) encodes a polypeptide of interest (P01) which may be all or part of a protein.

NOI1 and NOI2 (optionally together with subsequent NOI(s)) may encode a protein when transcribed and translated together. For example, The nucleic acid construct may be capable of producing two products when expressed in a cell:

a) a first product encoded by NOI1 alone; and
b) a second product, encoded by NOI1 and NOI2, which is produced when frame-slip or translational read-through occurs.

The relative level of expression of the full length product, encoded by NOI1 and NOI2 may be less than the level of expression of the truncated product, encoded by NOI1 alone.

Alternatively, the nucleic acid construct may comprise one or more cleavage site(s) so that the nucleotide sequences of interest are expressed as separate proteins.

The nucleic acid construct of the present invention may encode a polyprotein, which comprises first and second polypeptides. The polyprotein may be cleaved at a cleavage site to produce two discrete polypeptides.

An NOI may encode an intracellular, a transmembrane or a secreted protein.

An NOI may, for example, encode a chimeric antigen receptor (CAR) or part thereof, or an agent which affects the activity of a CAR or CAR-expressing cell, such as a cytokine.

The transgene may encode a target antigen. In this respect, the technology may be used to produce target antigens with varying and very low levels of target antigen. These may be used in functional assays for, for example, T cells expressing CARs or engineered T-cell receptors (TCRs).

The NOI may encode a protein involved in the synthesis of another entity by the cell. For example a cell can be induced to express the cancer antigen disialoganglioside (GD2) by the transgenic expression of two enzymes: GM3synthase and GD2synthase (WO2015/132604). By lowering the expression levels of these enzymes in the cell, it is possible to create $GD2^{low}$ target cells.

The NOI may encode a cytokine such as a cytokine which enhances the inflammatory response and/or increases the efficacy of CAR-T cell therapy. The cytokine may be selected from the following: IL-7, IL-12, IL15, IL-17A, IL-18 and IL-21. In particular, the cytokine may be IL-12.

Interleukin 12 (IL-12) is an interleukin that is naturally produced by dendritic cells, macrophages, neutrophils, and human B-lymphoblastoid cells in response to antigenic stimulation. IL-12 is involved in the differentiation of naive T cells into Th1 cells. It is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells, and reduces IL-4 mediated suppression of IFN-γ.

IL-12 plays an important role in the activities of natural killer cells and T lymphocytes. IL-12 mediates enhancement of the cytotoxic activity of NK cells and CD8+ cytotoxic T lymphocytes.

IL-12 is a potent immunomodulatory cytokine of particular interest for modulating the tumour microenvironment redirecting the immune response against cancer. IL-12 is systemically toxic therefore methods for producing IL-12 locally are of interest.

IL-12 is a heterodimeric cytokine encoded by two separate genes, IL-12A (p35) and IL-12B (p40). The active heterodimer (referred to as 'p70'), is formed following protein synthesis.

The NOI may encode IL-12A and/or IL-12B. The sequence for human IL-12A is available from Uniprot Accession number P29459. A portion of this sequence, lacking the signal peptide, is shown below as SEQ ID No. 53. The sequence for human IL-12B is available from Uniprot Accession number P29460. A portion of this sequence, lacking the signal peptide, is shown below as SEQ ID No. 54.

```
(human IL-12A)
                                         SEQ ID No. 53
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (human IL-12B)
                                         SEQ ID No. 54
WELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEP

KNKTFLRCEAKNYSGRFTCWWLTTISTDLTFSVKSSRGSSDPQGVTCGAA

TLSAERVRGDNKEYEYSVECQEDSACPAAEESLPIEVMVDAVHKLKYENY

TSSFFIRDIIKPDPPKNLQLKPLKNSRQVEVSWEYPDTWSTPHSYFSLTF

CVQVQGKSKREKKDRVFTDKTSATVICRKNASISVRAQDRYYSSSWSEWA

SVPC
```

The NOI may encode "flexi-IL-12", which is a fusion between the human IL-12α (p35) and IL-12β (p40) subunits, joined by a linker. A suitable flexi-IL-12 sequence is shown below as SEQ ID No. 55.

```
(a flexi-IL-12 sequence)
                                         SEQ ID No. 55
METDTLLLWVLLLWVPGSTGMWIWELKKDVYVVELDWYPDAPGEMVVLTC

DTPEEDGITWTLDQSSEVLGSGKTLTIQVKEFGDAGQYTCHKGGEVLSHS

LLLLHKKEDGIWSTDILKDQKEPKNKTFLRCEAKNYSGRFTCWWLTTIST

DLTFSVKSSRGSSDPQGVTCGAATLSAERVRGDNKEYEYSVECQEDSACP

AAEESLPIEVMVDAVHKLKYENYTSSFFIRDIIKPDPPKNLQLKPLKNSR

QVEVSWEYPDTWSTPHSYFSLTFCVQVQGKSKREKKDRVFTDKTSATVIC

RKNASISVRAQDRYYSSSWSEWASVPCSGGGGSGGGGSGGGGSRNLPLAT

PDPGMFPCLHHSQNLLRAVSNMLQKARQTLEFYPCTSEEIDHEDITKDKT

STVEACLPLELTKNESCLNSRETSFITNGSCLASRKTSFMMALCLSSIYE

DSKMYQVEFKTMNAKLLMDPKRQIFLDQNMLAVIDELMOALNFNSETVPQ

KSSLEEPDFYKTKIKLCILLHAFRIRAVTIDRVMSYLNAS
```

In SEQ ID No. 55, the signal peptide, which is the signal peptide from Murine kappa chain V-III region MOPC 63 (Uniprot P01661), is shown in bold; and the serine-glycine linker is in bold and underlined.

The NOI may comprise one of the sequence shown as SEQ ID No. 53, 54 or 55 or a variant thereof. The variant sequence may have at least 80, 85, 90, 95, 98 or 99% sequence identity to SEQ ID No. 53, 54 or 55, provided that the variant sequence retains IL-12 function when expressed in vivo. For example, the variant sequence may retain the capacity to enhance the activity of cytotoxic T cells in vivo and/or the variant sequence may stimulate the production of interferon-gamma (IFN-γ) by T cells.

A sequence encoding IL-12 or fliexi-IL12 may be placed downstream of a frame-slip motif or a translational readthrough motif. This provides a means of controlling cytokine expression and reducing the level of expression of cytokine relative to the CAR.

The NOI may encode a chemokine, for example a chemokine which improves the efficacy of CAR-T cell therapy. The chemokine may be CCL19. In particular, the nucleic acid construct may co-express CCL19 and IL-7.

The NOI may encode an antibody or part thereof. For example, the NOI may encode an immunomodulatory antibodies or antibody fragment. The antibody may block inhibitory signals (like PD1) or activate the immune system (such as OX40 agonistic agents, 41 BB agonistic agents or ICOS agonistic agents).

The transgene may encode a toxic compound such as Botulinum, Diptheria, or Pseudomonal toxin.

Chimeric Antigen Receptors

A classical chimeric antigen receptor (CAR) is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal-namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain.

A CAR may have the general structure:
Antigen binding domain-spacer domain-transmembrane domain-intracellular signaling domain (endodomain).

An NOI, or a combination of NOIs, of a nucleic acid construct of the invention may encode all or part of a CAR.

Functional readthrough can be exploited to increase the functionality of CARs. This can be achieved by inserting a translational readthrough motif downstream of the antigen-binding domain or between the signalling domains of the CAR (FIGS. 3F and F').

In some situations, it might be desirable to secrete an antigen-binding domain (scFv/VHH) to mitigate on-target off tumour effects where CAR T cells target normal tissue expressing low levels of a target antigen. The secreted antigen-binding domain would bind to the antigen expressed on the surface of the normal cell, thereby preventing recognition of the normal cell by the CAR T cell. Functional readthrough can be used to engineer T cells to secrete an antigen-binding domain by placing a translational readthrough motif immediately upstream of the transmembrane domain of the CAR.

The nucleic acid construct may have the general structure:
scFv/VHH-TRM-spacer-TM domain-endodomain, or
scFv/VHH-spacer-TRM-TM domain-endodomain
in which:
scFv/VHH is a nucleotide sequence encoding an antigen-binding domain spacer is a nucleotide sequence encoding a spacer
TM domain is a nucleotide sequence encoding a TM domain, and
endodomain is a nucleotide sequence encoding an endodomain, which may, for example, be a first, second or third generation endodomain.

Functional readthrough can also be used to generate combinations of CARs that are first, second or third generation. In this situation the translational readthrough motif may be placed in between the CD3z and the co-receptor endodomains, which results in a high level of expression of a first generation CAR (CD3ζ signalling domain alone) and a substantially lower level of the second or third generation CAR.

The nucleic acid construct may have the general structure:
scFv/VHH-spacer-TM domain-CD3ζ endodomain TRM-co-stimulatory domain, or
scFv/VHH-spacer-TM domain-CD3ζ endodomain TRM1-co-stimulatory domain1-TRM2-costimulatory domain 2
in which:
scFv/VHH is a nucleotide sequence encoding an antigen-binding domain
spacer is a nucleotide sequence encoding a spacer
TM domain is a nucleotide sequence encoding a TM domain, and
CD3ζ endodomain is a nucleotide sequence encoding a CD3ζ endodomain, and
Co-stimulatory domain is a nucleotide sequence encoding a co-stimulatory domain, such as the endodomain from a co-receptor such as CD28 or a member of the TNF receptor superfamily.

Different iterations can be generated by switching the position of the CD3ζ and co-receptor endodomains so that engagement of the CAR will provide predominantly a co-stimulatory signal (signal 2) to the cell and a reduced antigen signal (signal 1) to the cell, because fewer CARs would have both the co-receptor and CD3ζ signalling domains.

Chimeric Cytokine Receptors

WO2017/029512 describes chimeric cytokine receptors which graft the binding specificity of a non-cytokine binding molecule on to the endodomain of a cytokine receptor. It also describes a chimeric transmembrane protein comprising a dimerization domain; and a cytokine receptor endodomain.

Dimerisation may occur spontaneously, in which case the chimeric transmembrane protein will be constitutively active. Alternatively, dimerization may occur only in the presence of a chemical inducer of dimerization (CID) in which case the transmembrane protein only causes cytokine-type signalling in the presence of the CID.

A constitutively active chimeric cytokine receptor may comprise the Fab portion of an antibody as exodomain. In this respect, the dimerization domain may comprise the dimerization portion of a heavy chain constant domain (CH) and a light chain constant domain (CL).

The chimeric transmembrane protein may comprise two polypeptides:
(i) a first polypeptide which comprises:
  (a) a first dimerisation domain; and
  (b) a first chain of the cytokine receptor endodomain; and
(ii) a second polypeptide which comprises:
(a) a second dimerization domain, which dimerises with the first dimerization domain; and
(b) a second chain of the cytokine-receptor endodomain.

In particular, the chimeric transmembrane protein may comprise:
(i) a first polypeptide which comprises:
  (a) a heavy chain constant domain (CH)
  (b) a first chain of the cytokine receptor endodomain; and cells; and all three receptor chains form a complex that binds IL-2 with high affinity (Kd~10-11 M) on activated T cells and regulatory T cells.

The three IL-2 receptor chains span the cell membrane and extend into the cell, thereby delivering biochemical signals to the cell interior. The alpha chain does not participate in signalling, but the beta chain is complexed with the tyrosine phosphatase JAK1. Similarly the gamma chain complexes with another tyrosine kinase called JAK3. These enzymes are activated by IL-2 binding to the external domains of the IL-2R.

IL-2 signalling promotes the differentiation of T cells into effector T cells and into memory T cells when the initial T cells are also stimulated by an antigen. Through their role in the development of T cell immunologic memory, which depends upon the expansion of the number and function of antigen-selected T cell clones, they also have a key role in long-term cell-mediated immunity.

The chimeric cytokine receptor of the present invention may comprise the IL-2 receptor β-chain and/or the IL-2 receptor (i.e. common) γ-chain The amino acid sequences for the endodomains of the IL-2β-chain and common γ-chain are shown as SEQ ID No. 56 and 57

```
SEQ ID No. 56: Endodomain derived from human common gamma chain:
ERTMPRIPTLKNLEDLVTEYHGNFSAWSGVSKGLAESLQPDYSERLCLVSEIPPKGG

ALGEGPGASPCNQHSPYWAPPCYTLKPET

SEQ ID No. 57: Endodomain derived from human IL-2Rβ:
NCRNTGPWLKKVLKCNTPDPSKFFSQLSSEHGGDVQKWLSSPFPSSSFSPGGLAP

EISPLEVLERDKVTQLLLQQDKVPEPASLSSNHSLTSCFTNQGYFFFHLPDALEIEAC

QVYFTYDPYSEEDPDEGVAGAPTGSSPQPLQPLSGEDDAYCTFPSRDDLLLFSPSL

LGGPSPPSTAPGGSGAGEERMPPSLQERVPRDWDPQPLGPPTPGVPDLVDFQPP

PELVLREAGEEVPDAGPREGVSFPWSRPPGQGEFRALNARLPLNTDAYLSLQELQ

GQDPTHLV
```

(ii) a second polypeptide which comprises:
  (a) a light chain constant domain (CL)
  (b) a second chain of the cytokine-receptor endodomain.

The first and second chains for the cytokine receptor endodomains may be selected from type I cytokine receptor endodomain α-, β-, and γ-chains.

The cytokine receptor endodomain may comprise:
(i) IL-2 receptor β-chain endodomain
(ii) IL-7 receptor α-chain endodomain; or
(iii) IL-15 receptor α-chain endodomain; and/or
(iv) common γ-chain receptor endodomain.
IL-2

IL-2 binds to the IL-2 receptor, which has three forms, generated by different combinations of three different proteins, often referred to as "chains": α, β and γ; these subunits are also parts of receptors for other cytokines. The β and γ chains of the IL-2R are members of the type I cytokine receptor family.

The three receptor chains are expressed separately and differently on various cell types and can assemble in different combinations and orders to generate low, intermediate, and high affinity IL-2 receptors.

The α chain binds IL-2 with low affinity, the combination of β and γ together form a complex that binds IL-2 with intermediate affinity, primarily on memory T cells and NK The term "derived from" means that the endodomain of the chimeric cytokine receptor of the invention has the same sequence as the wild-type sequence of the endogenous molecule, or a variant thereof which retains the ability to form a complex with JAK-1 or JAK-3 and activate one of the signalling pathways mentioned above.

A "variant" sequence having at least 80, 85, 90, 95, 98 or 99% sequence identity to the wild-type sequence (e.g. SEQ ID Nos. 56 or 57), providing that the variant sequence retains the function of the wild-type sequence i.e. the ability to form a complex with JAK-1 or JAK-3 and activate, for example, the JAK-STAT signalling pathway.

The percentage identity between two polypeptide sequences may be readily determined by programs such as BLAST which is freely available at http://blast.ncbi.nlm.nih.gov.

Constant Region Domains

There are two types of light chain in humans: kappa (κ) chain and lambda (λ) chain. The lambda class has 4 sub-types: λ1, λ2, λ3 and λ4. The light chain constant region of a Fab-type chimeric receptor may be derived from any of these light chain types.

The light chain constant domain of a chimeric cytokine receptor may have the sequence shown as SEQ ID NO. 58 which is a kappa chain constant domain.

SEQ ID No. 58
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

There are five types of mammalian immunoglobulin heavy chain: γ, δ, α, μ and ε which define the classes of immunoglobulin IgG, IgD, IgA, IgM and IgE respectively. Heavy chains γ, δ and α have a constant domain composed of three tandem Ig domain and have a hinge for added flexibility. Heavy chains μ and ε are composed of four domains.

The CH domain of a chimeric cytokine receptor of the present invention may comprise the sequence shown as SEQ ID No. 59 which is from a γ immunoglobulin heavy chain.

SEQ ID No. 59
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRV

In a preferred embodiment, the present invention provides a nucleic acid construct comprising: a first nucleotide sequence encoding a chimeric antigen receptor (CAR); a frame-slip motif (FSM) or a translational readthrough motif (TRM); and a second nucleotide sequence encoding a chimeric cytokine receptor (CCR).

Cleavage Site

The nucleic acid construct of the first aspect of the invention may comprise a sequence encoding a cleavage site positioned between nucleic acid sequences which encode first and second polypeptides, such that first and second polypeptides can be expressed as separate entities.

The cleavage site may be any sequence which enables the polypeptide comprising the first and second polypeptides to become separated.

The term "cleavage" is used herein for convenience, but the cleavage site may cause the first and second polypeptidess to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode first and second polypeptides, causes the first and second polypeptides to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg' (SEQ ID No. 50)) and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (SEQ ID No. 51) (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the first and second polypeptides and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus.

The C-terminal 19 amino acids of the longer cardiovirus protein, together with the N-terminal proline of 2B mediate "cleavage" with an efficiency approximately equal to the apthovirus FMDV 2a sequence. Cardioviruses include encephalomyocarditis virus (EMCV) and Theiler's murine encephalitis virus (TMEV).

Mutational analysis of EMCV and FMDV 2A has revealed that the motif DxExNPGP (SEQ ID No. 52) is intimately involved in "cleavage" activity (Donelly et al (2001) as above).

The cleavage site of the present invention may comprise the amino acid sequence: $Dx_1Ex_2NPGP$, where $x_1$ and $x_2$ are any amino acid. $X_1$ may be selected from the following group: I, V, M and S. $X_2$ may be selected from the following group: T, M, S, L, E, Q and F.

For example, the cleavage site may comprise one of the amino acid sequences shown in Table 2.

TABLE 2

| Motif | Present in: |
|---|---|
| DIETNPGP (SEQ ID No. 46) | Picornaviruses EMCB, EMCD, EMCPV21 |
| DVETNPGP (SEQ ID No. 47) | Picornaviruses MENGO and TMEBEAN; Insect virus DCV, ABPV |
| DVEMNPGP (SEQ ID No. 48) | Picornaviruses TMEGD7 and TMEBEAN |
| DVESNPGP (SEQ ID No. 49) | Picornaviruses FMDA10, FMDA12, FMDC1, FMD01K, FMDSAT3, FMDVSAT2, ERAV; Insect virus CrPV |
| DMESNPGP (SEQ ID No. 12) | Picornavirus FMDV01G |

TABLE 2 -continued

| Motif | | Present in: |
|---|---|---|
| DVELNPGP | (SEQ ID No. 13) | Picornavirus ERBV; Porcine rotavirus |
| DVEENPGP | (SEQ ID No. 14) | Picornavirus PTV-1; Insect virus TaV; Trypanosoma TSR1 |
| DIELNPGP | (SEQ ID No. 15) | Bovine Rotavirus, human rotavirus |
| DIEQNPGP | (SEQ ID No. 16) | Trypanosoma AP endonuclease |
| DSEFNPGP | (SEQ ID No. 17) | Bacterial sequence T. maritima |

The cleavage site, based on a 2A sequence may be, for example 15-22 amino acids in length. The sequence may comprise the C-terminus of a 2A protein, followed by a proline residue (which corresponds to the N-terminal proline of 2B).

Mutational studies have also shown that, in addition to the naturally occurring 2A sequences, some variants are also active. The cleavage site may correspond to a variant sequence from a naturally occurring 2A polypeptide, have one, two or three amino acid substitutions, which retains the capacity to induce the "cleavage" of a polyprotein sequence into two or more separate proteins.

The cleavage sequence may be selected from the following which have all been shown to be active to a certain extent (Donnelly et al (2001) as above):

```
                                 (SEQ ID No. 18)
LLNFDLLKLAGDVESNPGP (SEQ ID No. 19)
LLNFDLLKLAGDVQSNPGP (SEQ ID No. 20)
LLNFDLLKLAGDVEINPGP (SEQ ID No. 21)
LLNFDLLKLAGDVEFNPGP (SEQ ID No. 22)
LLNFDLLKLAGDVESHPGP (SEQ ID No. 23)
LLNFDLLKLAGDVESEPGP (SEQ ID No. 24)
LLNFDLLKLAGDVESQPGP (SEQ ID No. 25)
LLNFDLLKLAGDVESNPGG
```

Based on the sequence of the DxExNPGP "a motif, "2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2A-like sequences, such as:

```
                                 (SEQ ID No. 26)
YHADYYKQRLIHDVEMNPGP (SEQ ID No. 27)
HYAGYFADLLIHDIETNPGP (SEQ ID No. 28)
QCTNYALLKLAGDVESNPGP (SEQ ID No. 29)
ATNFSLLKQAGDVEENPGP (SEQ ID No. 30)
AARQMLLLLSGDVETNPGP (SEQ ID No. 31)
RAEGRGSLLTCGDVEENPGP (SEQ ID No. 32)
TRAEIEDELIRAGIESNPGP (SEQ ID No. 33)
TRAEIEDELIRADIESNPGP (SEQ ID No. 34)
AKFQIDKILISGDVELNPGP (SEQ ID No. 35)
SSIIRTKMLVSGDVEENPGP (SEQ ID No. 36)
CDAQRQKLLLSGDIEQNPGP (SEQ ID No. 37)
YPIDFGGFLVKADSEFNPGP
```

The cleavage site may comprise the 2A-like sequence shown as SEQ ID No. 31 (RAEGRGSLLTCGDVEENPGP).

It has been shown that including an N-terminal "extension" of between 5 and 39 amino acids can increase activity (Donnelly et al (2001) as above). In particular, the cleavage sequence may comprise one of the following sequences or a variant thereof having, for example, up to 5 amino acid changes which retains cleavage site activity:

```
                                               (SEQ ID No. 38)
VTELLYRMKRAETYCPRPLAIHPTEARHKQKIVAPVKQTLNFDLLKLAGD
VESNPGP (SEQ ID No. 39)
LLAIHPTEARHKQKIVAPVKQTLNFDLLKLAGDVESNPGP (SEQ ID No. 40)
EARHKQKIVAPVKQTLNFDLLKLAGDVESNPGP (SEQ ID No. 41)
APVKQTLNFDLLKLAGDVESNPGP
```

Vector

The present invention also provides a vector comprising a nucleic acid construct according to the first aspect of the invention.

Such a vector may be used to introduce the nucleic acid construct into a host cell so that it expresses the first and second polypeptide.

The vector may, for example, be a plasmid or a viral vector, such as a retroviral vector or a lentiviral vector, or a transposon based vector or synthetic mRNA.

The vector may be capable of transfecting or transducing a mammalian cell, for example a T cell or a target cell.

Cell

The present invention furthers provides a cell comprising a nucleic acid construct or vector of the present invention which expresses the first and second polypeptide encoded by the nucleic acid sequence.

The cell may be any eukaryotic cell such as an immunological cell.

The cell may be a cytolytic immune cell, such as a T cell or natural killer cell.

Where the transgene expresses a target antigen, the cell may be a target cell for a T cell or CAR-T cell.

Method

In a further aspect, the present invention provides a method for making a cell according to the invention which comprises the step of introducing a nucleic acid construct or a vector of the invention into a cell.

The nucleic acid construct may be introduced by transduction or transfection.

The cell may be a cell isolated from a subject, for example a T cell or an NK cell isolated from a subject.

The present invention also provides a method for modulating the relative expression of two transgenes in a nucleic acid construct which comprises the step of including a frame-slip motif or a translational readthrough motif between the two transgenes in order to reduce the expression of the downstream transgene.

The nucleic acid construct may comprise a sequence encoding a cleavage site, positioned between the two transgenes. The relative expression of the two transgenes may be tuned by choosing different frame-slip motifs or translational readthrough motifs and/or by mutating the sequence immediately 5' and/or 3' to the motif.

chimeric protein having a CD22 ectodomain and a CD19 transmembrane and endodomain.

The first construct comprises a transcriptional frame-slip which has seven thymine bases (uracil in mRNA) that promote transcriptional slippage and the loss of a base from the mRNA, which places the CD22 coding sequence in frame and results in expression of the CD22-CD19 chimera.

Flow cytometric analysis showed that introduction of the frame-slip motif resulted in dramatically reduced expression of the CD22-CD19 chimera while similar levels of the RQR8 sort selection marker were observed (FIG. 2C).

Example 2—Making and Testing a Translational Readthrough Construct

The two translational readthrough motifs, STOP-CUAG and STOP-CAAUUA, were shown to be functional in human T cells (SupT1) and human B cells (Raji) and to support translational readthrough of a downstream self-cleaving 2A peptide sequence and transgene coding sequence (CD22 and BCMA).

In order to test the function of these readthrough motifs in combination with different stop codons, the following constructs were transduced into HEK293T cells.

```
Readthrough motif STOP-CUAG
SFGmR.RQR8-STOP-TGACTAG-2A-hCD22ecto-CD19TM-dCD19endo SFGmR.RQR8-STOP-TAGCTAG-2A-hCD22ecto-CD19TM-dCD19endo SFGmR.RQR8-STOP-TAACTAG-2A-hCD22ecto-CD19TM-dCD19endo SFGmR.RQR8-NO_STOP_TGGCTAG-T2A-hCD22ecto-CD19TM-dCD19endo Readthrough motif STOP-CAAUUA
SFGmR.RQR8-STOP-TGACAATTA-2A-hCD22ecto-CD19TM-dCD19endo SFGmR.RQR8-STOP-TAGCAATTA-2A-hCD22ecto-CD19TM-dCD19endo SFGmR.RQR8-STOP-TAACAATTA-2A-hCD22ecto-CD19TM-dCD19endo SFGmR.RQR8_NO_STOP_TGGCAATTA-T2A-hCD22-CD19TM-dCD19endo
```

The invention also provides method for modulating the relative expression of two transgenes in a nucleic acid construct, which comprises the step of including a frame-slip motif or a translational readthrough motif between the two transgenes in order to reduce the expression of the downstream transgene.

The frame-slip motif or a translational readthrough motif may be as described in the previous aspects of the invention.

The invention will now be further described by way of Examples, which are meant to serve to assist one of ordinary skill in the art in carrying out the invention and are not intended in any way to limit the scope of the invention.

EXAMPLES

Example 1—Making and Testing a Frame-Slip Construct

The following constructs were transduced into SupT1 cells.
SFGmR.RQR8-2A-SKIP 7xU-CD22ecto-CD19tm-dCD19endo
SFGmR.RQR8-2A-SKIP_6xU-CD22ecto-CD19tm-dCD19endo (control)

The constructs encode RQR8, a sort-suicide transmembrane protein which is described in WO2013/153391; and a Signal peptide mutants
SFGmR.RQR8-2A-signal K9-hCD22ecto-CD19TM-dCD19endo
SFGmR.RQR8-2A-signal K10-hCD22ecto-CD19TM-dCD19endo
SFGmR.RQR8-2A-signal K11-hCD22ecto-CD19TM-dCD19endo The wild-type signal peptide sequence together with the sequences of the altered signal peptides K19, K10 and K11 are shown below as SEQ ID Nos. 42 to 45.

```
SEQ ID No. 42 - murine Ig kappa chain VIII
region signal peptide (wild-type)
METDTLILWVLLLLVPGSTG SEQ ID No. 43 - murine Ig kappa chain VIII
region signal peptide (K9 mutant)
METDTLILKVLLLLVPGSTG SEQ ID No. 44 - murine Ig kappa chain VIII
region signal peptide (K10 mutant)
METDTLILWKLLLLVPGSTG SEQ ID No. 45 - murine Ig kappa chain VIII
region signal peptide (K11 mutant)
METDTLILWVKLLLVPGSTG
```

Figure 4A:
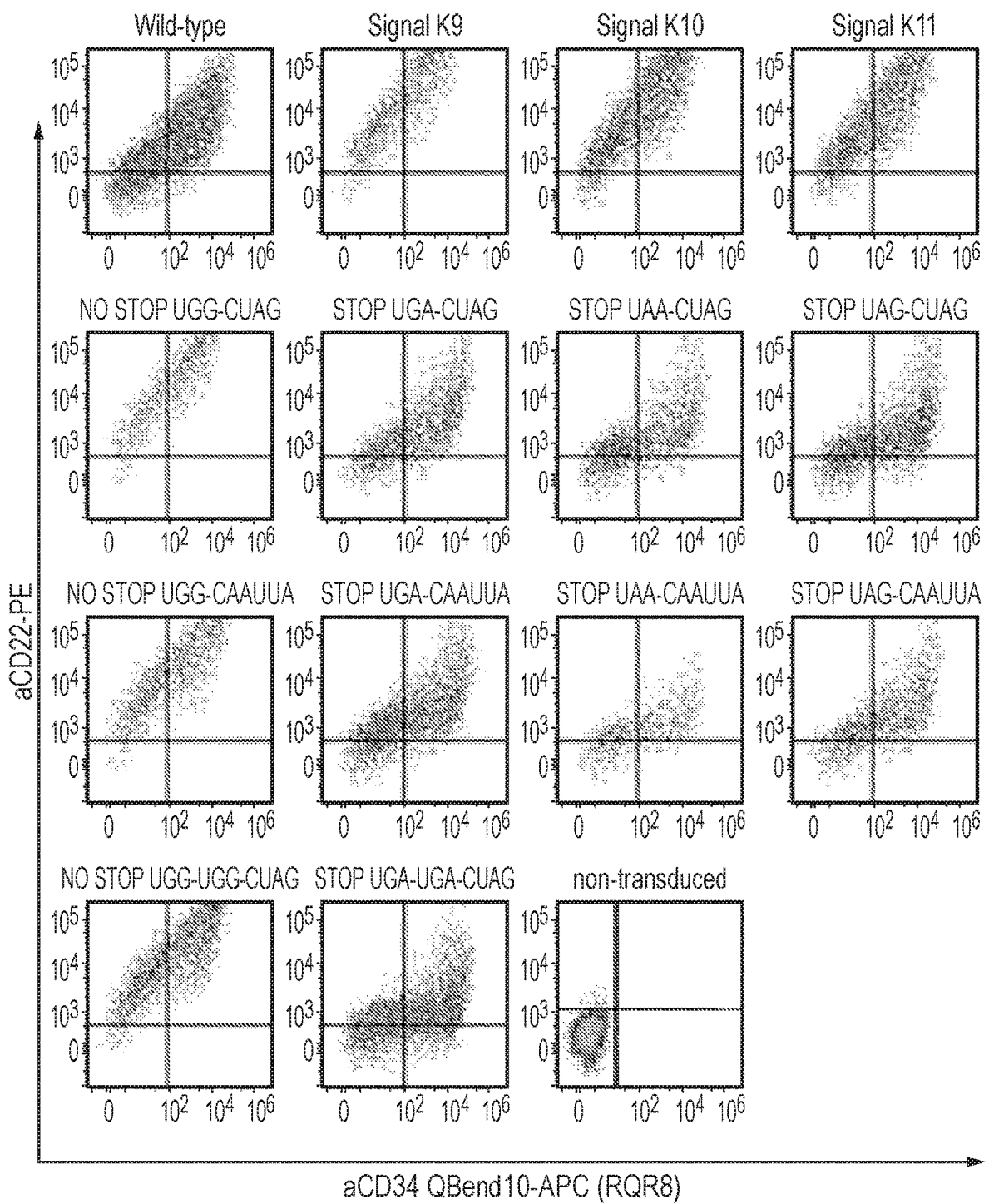
FIG. 4: Comparison of attenuated signal peptide and translational readthrough motif approaches for controlling expression of a CD22-CD19 chimera.
(A) Flow cytomteric analysis of HEK293T cells transfected with constructs encoding the RQQ8 sort selection marker and a CD22-CD19 chimera. Signal peptide mutants (1st row), translational readthrough motif construct (2nd and 3rd rows) and a double stop translational readthrough motif (4th row). Compared to the wild-type signal peptide, expression of the CD22-CD19 chimera is reduced in the lysine 11 signal peptide mutant (L11K mutation). The stop-CUAG and stop-CAAUUA translational readthrough motif yield similar results when they are placed 5' to the CD22-CD19 transgene, with both motifs reducing the level of expression of the chimera to approximately 2% or less of the RQR8 sort selection marker. Lower expression levels of the CD22-CD19 chimera were obtained using the double stop translational readthrough motif (4th row). (B) Quantification of the mean fluorescence intensity of the CD22-CD19 chimera on the surface of transfected HEK293T cells, comparing the attenuated signal peptide mutants to the translational readthrough constructs. Substantially lower levels of CD22-

Expression of the CD22-CD19 chimera was analysed by flow cytometry and the results are shown in FIG. 4A. Compared to the wild-type signal peptide, expression of the CD22-CD19 chimera was reduced in the lysine 11 signal peptide mutant (L11K mutation). The stop-CUAG and stop-CAAUUA translational readthrough motif yielded similar results when they were placed 5' to the CD22-CD19 transgene, with both motifs reducing the level of expression of the chimera to approximately 2% or less of the RQR8 sort selection marker. Lower expression levels of the CD22-CD19 chimera were obtained using the double stop translational readthrough motif (4th row).

Figure 4B:
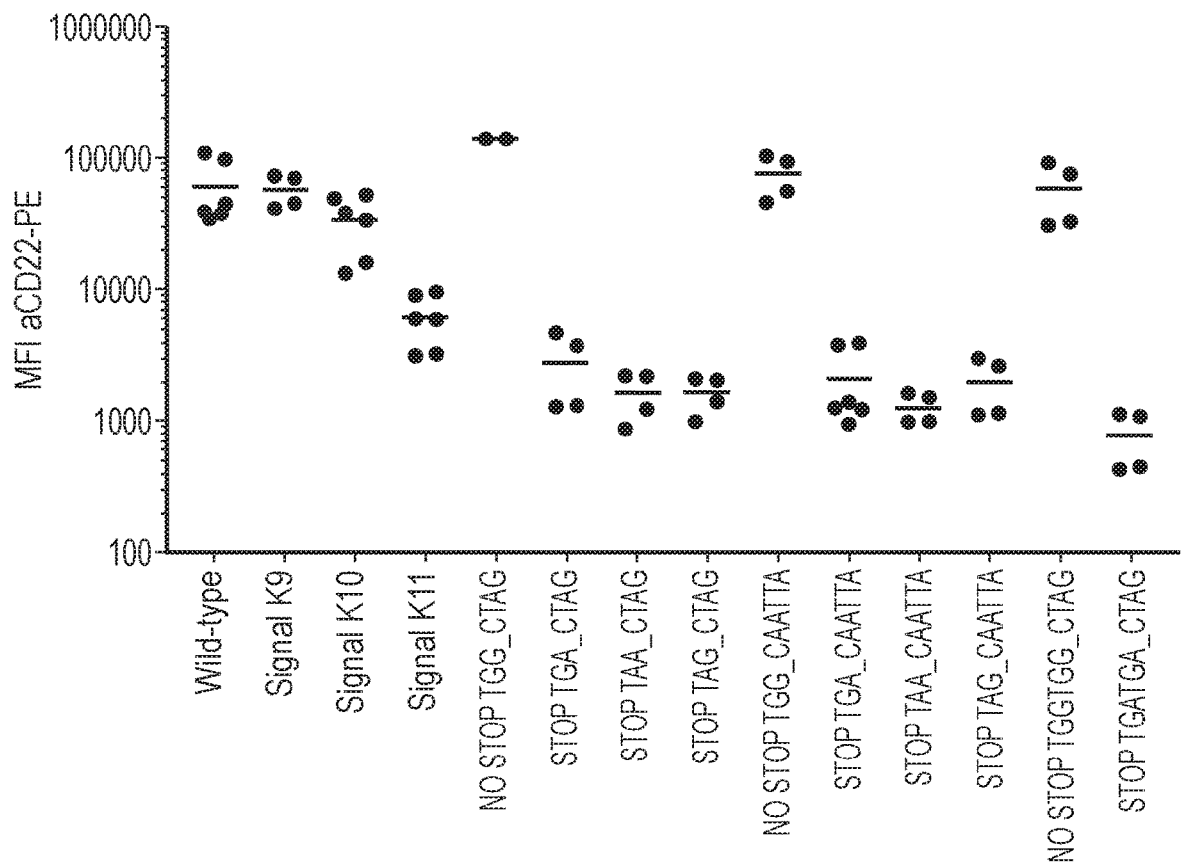

The mean fluorescence intensity of the CD22-CD19 chimera was quantified on the surface of transfected HEK293T cells and the results are shown in FIG. 4B. Substantially lower levels of CD22-CD19 chimera were obtained using the translational readthrough constructs compared to the attenuated signal peptide mutants.

Example 3—Functional Translational Readthrough: Secretion of Soluble Anti-CD22 Fab Nucleic acid constructs were designed which encode the RQR8 sort selection marker followed by a 2A self-cleaving peptide sequence and an anti-CD22 CAR with CL and CH1 spacer regions to produce a soluble Fab fragment, as shown below:

SFGmR.RQR8-2A-aCD22 FabCAR_9A8-1-STOP_SKIP_TAG-41BBz
SFGmR.RQR8-2A-aCD22 FabCAR_9A8-1-STOP_SKIP_TAA-41BBz
SFGmR.RQR8-2A-aCD22 FabCAR_9A8-1-STOP_SKIP_TGA-41BBz

These constructs are transduced into PBMCs and cytotoxicity assays are carried out using target cells expressing a low or high level of CD22 to determine the efficacy of the CARs. This mimics a situation where a low level of the target antigen is expressed on normal tissue and fine-tuning of the cytotoxic response is required to prevent CAR T cells from targeting these cells.

Example 4—Functional Translational Readthrough: Switching from 1st Generation to 2nd or 3rd Generation CARs To investigate whether functional translational readthrough can be used to switch switching between a first and a second generation CAR, the following constructs are generated:

SFGmR.RQR8-2A-aCD19fmc63-HCH2CH3pvaa-Zeta
SFGmR.RQR8-2A-aCD19fmc63-HCH2CH3pvaa-Zeta-STOP_SKIP_TAA-41BB
SFGmR.RQR8-2A-aCD19fmc63-HCH2CH3pvaa-Zeta-STOP_SKIP_TGA-41BB
SFGmR.RQR8-2A-aCD19fmc63-HCH2CH3pvaa-Zeta-NO_STOP_SKIP_TCA-41BB
SFGmR.RQR8-2A-aCD19fmc63-HCH2CH3pvaa-Zeta-STOP_SKIP_TAG-41BB
SFGmR.RQR8-2A-aCD19fmc63-HCH2CH3pvaa-Zeta-STOP_SKIP_TAA-CD28
SFGmR.RQR8-2A-aCD19fmc63-HCH2CH3pvaa-Zeta-STOP_SKIP_TAG-CD28
SFGmR.RQR8-2A-aCD19fmc63-HCH2CH3pvaa-Zeta-NO_STOP_SKIP_TCA-CD28
SFGmR.RQR8-2A-aCD19fmc63-HCH2CH3pvaa-Zeta-STOP_SKIP_TGA-CD28

This first set of constructs express the sort selection marker RQR8 and a first generation anti-CD19 CAR with an Fc spacer domain and a CD3ζ endodomain followed by a translational readthrough motif and a 4-1BB or CD28 co-stimulatory endodomain. Restimulation assays are set up using transduced PBMCs, which are cultured in plates coated with an anti-Fc antibody that bind to the spacer domain of the CARs and trigger proliferation. The control first generation CAR, which has only a CD3ζ exhibits limited proliferation, while the other CARs proliferate to a greater extent as a co-stimulatory signal is present.

A second set of constructs, similar to the first, is generated as shown below:

SFGmR.RQR8-2A-aCD19fmc63-HCH2CH3pvaa-41BB-STOP_SKIP_TAA-Zeta
SFGmR.RQR8-2A-aCD19fmc63-HCH2CH3pvaa-41BB-STOP_SKIP_TGA-Zeta
SFGmR.RQR8-2A-aCD19fmc63-HCH2CH3pvaa-41BB-NO_STOP_SKIP_TCA-Zeta
SFGmR.RQR8-2A-aCD19fmc63-HCH2CH3pvaa-41BB-STOP_SKIP_TAG-Zeta
SFGmR.RQR8-2A-aCD19fmc63-HCH2CH3pvaa-CD28-STOP_SKIP_TAA-Zeta
SFGmR.RQR8-2A-aCD19fmc63-HCH2CH3pvaa-CD28-STOP_SKIP_TGA-Zeta
SFGmR.RQR8-2A-aCD19fmc63-HCH2CH3pvaa-CD28-NO_STOP_SKIP_TCA-Zeta
SFGmR.RQR8-2A-aCD19fmc63-HCH2CH3pvaa-CD28-STOP_SKIP_TAG-Zeta In these constructs, a co-stimulatory domain from 4-1 BB or CD28 lies before the translational readthrough motif and the CD3ζ endodomain is placed afterwards. Cytotoxicity assays and proliferation assays are set up using PBMCs transduced with these constructs. Translation readthrough from these constructs is necessary to produce a functional CAR (i.e. a CAR with an intracellular signalling domain).

Example 5—Making and Testing a Compound Readthrough Motifs

In order to reduce the expression of multi-transgene cassettes to exceptionally low levels, a construct was designed having two STOP-translational readthrough motifs, as follows:
Marker (RQR8 or HA8)STOP_readthrough-2A-GD3 synthase-STOP_readthrough-2A-GD2 synthase The ganglioside GD2 is synthesised by two enzymes GD2 and GD3 synthase. The construct above gives reduced expression of GD3 synthase compared to the marker gene and even lower expression of GD2 synthase.

Example 6—Making and Testing a Universal Readthrough Construct

To overcome problems with context-dependent expression from the readthrough motifs, a set of universal constructs are generated into which a second transgene can be cloned at expressed at defined levels. The universal constructs consist of a self-cleaving 2A peptide sequence followed by a stop codon and readthrough motif and a second self-cleaving peptide sequence. Flanking the stop readthrough motifs with self-cleaving peptide sequences reduces the context dependents effects on translational readthrough and produces consistent and predictable levels of transgene expression.

The constructs tested are as follows:

```
Readthrough motif STOP CUAG
Marker-2A-Transgene 1-2A-UGA-CUAG-2A-Transgene 2

Marker-2A-Transgene 1-2A-UAG-CUAG-2A-Transgene 2

Marker-2A-Transgene 1-2A-UAA-CUAG-2A-Transgene 2

Readthrough motif STOP CAAUUA
Marker-2A-Transgene 1-2A-UGA-CAAUUA-2A-Transgene 2

Marker-2A-Transgene 1-2A-UAG-CAAUUA-2A-Transgene 2

Marker-2A-Transgene 1-2A-UAA-CAAUUA-2A-Transgene 2
```

Example 7—Ultra-Low Expression by Placing Translational Readthrough Motifs in Series To determine whether it was possible to obtain an ultra-low level of transgene expression, constructs were generated where two translational readthrough motifs were placed in series in a tri-cistronic cassette (FIG. 5A). The first transgene in the cassette was always a cell surface marker, consisting of an HA epitope presented on a CD8a stalk, for the identification of transduced cells followed by a stop codon, translational readthrough motif and a self-cleaving peptide sequence. The second transgene in the cassette was one of two fluorescent proteins, either tandem Clover3 (green fluorescent protein) or enhanced blue fluorescent protein (EBFP), which was followed by a stop codon, translational readthrough motif and self-cleaving peptide sequence. The third transgene in the cassette was the alternate fluorescent protein. By placing the stop codons and translational readthrough motifs in series, the expression level of the fluorescent protein in the third position should be lower than that of the second.

Peripheral blood mononuclear cells (PBMCs) were transduced with the constructs and flow cytometry carried to quantify the expression level of the fluorescent proteins relative to the cell surface marker. The results of these experiments demonstrated that expression levels of the fluorescent proteins were significantly lower when placed in the third position, downstream of two stop codons and translational readthrough motifs, than when placed in the second position (FIG. 5B). In agreement with previous experiments, the level of translational readthrough was dependent on the stop codon with the hierarchy stop codon stringency being UAA>UAG>UGA. In the case of tandem Clover3, the reduction in the level of expression, compared to a no stop control, was 33-fold for UAA, 24-fold for UAG and 6-fold for UGA. When placed in the third position the level of tandem Clover3 expression was reduced >100-fold for all three stop codons (FIG. 5C).

Example 8—Control of IL-12 Secretion by Translational Readthrough

IL-12 is a potent proinflammatory cytokine that is secreted by phagocytes and dendritic cells in response to pathogens, signals from T-cells and natural killer (NK) and components of the inflammatory extracellular matrix. The main targets of IL-12 are cytotoxic T cells, $T_H1$ helper T cells and NK cells, which express the IL-12 receptor on their cell surface. In response to IL-12, $T_H1$ helper T cells release IFNγ and TNFα.

CAR-T cells have been engineered to express IL-12 constitutively or from an inducible promoter and this has been shown to improve the efficacy of CAR-T cell therapy when targeting solid tumours. Administration of IL-12 systemically is toxic and to circumvent this problem CAR T-cells or other immune cells have been engineered to release IL-12 into the tumour microenvironment. However, transgenic T-cell IL-12 secretion can result in highly toxic systemic levels of the cytokine.

We designed constructs where a fusion between the human IL-12α (p35) and IL-12β (p40) subunits, flexi-IL-12, was cloned downstream of the sort select marker RQR8 and a self-cleaving peptide sequence. A stop codon or control sequence (UGG encoding tryptophan) and the translational readthrough sequence CAAUUA were placed immediately downstream of the RQR8 coding sequence (FIG. 6A). PBMCs were transduced with the constructs and stained with antibodies to CD3ε and RQR8 to determine the transduction efficiency and verify the presence of the transgenes (FIG. 6B). After determining transduction efficiency, the PBMCs were placed back into culture and supernatant collected at 24, 48 and 72 hours and analysed for the presence of IL-12 by high sensitivity ELISA (FIG. 6C). The data demonstrated that inclusion of a stop codon and translational readthrough motif reduced the level by more than 40-fold (FIG. 6C). There was a trend in the hierarchy of stop codon stringency with the order of most stringent to least being UAA>UAG>UGA. These data demonstrated that it was possible to significantly reduce the level of IL-12 secretion from transduced cells.

To demonstrate that the secreted levels of flexi-IL-12 were able to trigger immune responses, we generated another set of constructs. These were tri-cistronic constructs containing a suicide gene (RapaCasp9), the murine cell surface marker Thy1.1 and murine flexi-IL-12 (FIG. 7A). The murine flexi-IL-12 sequence was positioned at the end of the tri-cistronic cassette and self-cleaving peptides sequences were used to facilitate expression of the polypeptides. The translation readthrough construct (UAA-CAAUUA) was compared to a construct containing murine flexi-IL-12 with an attenuated signal peptide sequence and another utilising an internal ribosome entry site (IRES) to control expression of the cytokine. Splenocytes obtained from BalbC mice were transduced with the constructs and flow cytometry carried out using antibodies to CD3 and the cell surface marker Thy1.1 to determine transduction efficiency (FIG. 7B). After determining transduction efficiency, the splenocytes were placed back in culture and supernatant collected at 24, 48 and 72 hours and analysed for the presence of murine IL-12 by ELISA (FIG. 7C). The results demonstrated that expression of IL-12 from the IRES was reduced approximately 3-fold. In contrast, expression of IL-12 from the translational readthrough motif UAA-CAAUUA was reduced to the point where it was no longer detectable by ELISA (FIG. 7C). To ascertain if IL-12 was present in the culture medium, supernatants were recovered and used to re-stimulate activated splenocytes. Supernatant from these re-stimulated splenocytes was analysed for the presence of IFNγ, as this is secreted by T cells and NK cells stimulated with IL-12 (FIG. 7D). IFNγ was detectable in all the supernatants harvested from the re-stimulated splenocytes. In accordance with the results of the IL-12 ELISA the highest levels of IFNγ secretion were observed from splenocytes re-stimulated with supernatant from control or IRES transduced splenocytes. Importantly, secretion of IFNγ was observed from splenocytes re-stimulated with supernatant derived from splenocytes transduced with the translational readthrough construct (FIG. 7D). These results demonstrated that it was possible to obtain significantly reduced levels of IL-12 secretion from transduced cells, potentially mitigating the toxic effects of this potent cytokine while still maintaining therapeutic benefit.

To demonstrate efficacy and safety profile of IL-12 secretion from the translational readthrough construct in a more therapeutic setting, splenocytes were co-transduced with a construct encoding truncated murine CD34, an anti-GD2 chimeric antigen receptor and firefly luciferase and the cytokine expression constructs described before. Transduced splenocytes were stained with antibodies to CD34 and Thy1.1 and analysed by flow cytometry to determine transduction efficiency (FIG. 8A). Mice were injected with the $5 \times 10^6$ transduced splenocytes and 15 days later the mice were sacrificed and their spleens removed. Comparison of spleen size indicated that splenomegaly was only observed where IL-12 was constitutively expressed (2A), while the spleen size in the other groups was comparable with the control (FIG. 8B). To investigate in more detail the cell types recruited to the spleens of injected mice, splenocytes were stained with antibodies to CD11 b, CD3, CD4, CD8 and CD19 and analysed by flow cytometry (FIG. 9A). The results indicated the recruitment of macrophages (CD11b$^+$) to the spleens of mice injected with splenocytes transduced with constitutively expressed IL-12 with approximately 20% cells being CD11b$^+$. In agreement with previous ELISA data showing that the IRES construct produced a higher level of IL-12 than the translational readthrough construct, more CD11b$^+$ cells were present in the spleens of mice injected with these cells (FIG. 9B). Increased recruitment of T cells, both CD4$^+$ and CD8$^+$, was observed in mice injected with splenocytes transduced with constructs constitutively expressing IL-12 or from an IRES (FIGS. 9C, D and E). In contrast, the numbers of CD11b$^+$ and CD3$^+$ cells in the spleens of mice injected with splenocytes transduced with the translational readthrough construct were comparable to the control. A reduction in B-cell numbers was only observed in spleens from mice injected with splenocytes constitutively expressing IL-12. Together these results suggested that expression of IL-12 from the translational readthrough construct did not cause any toxicity or recruitment of immune cells in the absence of antigen.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A nucleic acid construct comprising:
   a first nucleotide sequence of interest (NOI1), a translational readthrough motif (TRM), and a second nucleotide sequence of interest (NOI2), and
   a nucleotide sequence encoding a cleavage site (CL), so that NOI1 and NOI2 are expressed as separate proteins, wherein the (TRM) comprises the sequence STOP-CUAG or STOP-CAAUUA, in which "STOP" is a stop codon.

2. A nucleic acid construct according to claim 1, wherein the translational readthrough motif comprises one or more of the follow sequences:

```
UGA-CUAG       (SEQ ID No. 5)

UAG-CUAG       (SEQ ID No. 6)

UAA-CUAG       (SEQ ID No. 7)

UGA-CAAUUA     (SEQ ID No. 8)

UAG-CAAUUA     (SEQ ID No. 9)

UAA-CAAUUA.    (SEQ ID No. 10)
```

3. A nucleic acid construct according to claim 1 which has the structure:
   NOI1-TRM-CL-NOI2,
   NOI1-TRM1-TRM2-CL-NOI2,
   NOI1-CL1-TRM-CL2-NOI2,
   NOI1-TRM-CL-SP-NOI2,
   NOI1-TRM1-CL1-NOI2-TRM2-CL2-NOI3, or
   NOI1-TRM1-CL1-TRM2-CL2-NOI2,
   in which:
   TRM1 and TRM2, which may be the same or different, are first and second translational readthrough motifs;
   CL1 and CL2, which may be the same or different, are first and second nucleic acid sequences each encoding a cleavage site,
   SP is an attenuated signal peptide, and
   NOI3 is a third nucleotide sequence of interest.

4. A nucleic acid construct according to claim 1 wherein the cleavage site comprises a self-cleaving peptide, a furin cleavage site or a Tobacco Etch Virus cleavage site.

5. A nucleic acid construct according to claim 4, wherein the cleavage site comprises a 2A self-cleaving peptide from an aphtho- or a cardiovirus or a 2A-like peptide.

6. A vector comprising a nucleic acid construct according to claim 1.

7. A retroviral vector or a lentiviral vector according to claim 6.

8. A cell comprising a nucleic acid construct according to claim 1.

9. A method for making a cell according to claim 8 which comprises the step of introducing into a cell a nucleic acid construct comprising:
   a first nucleotide sequence of interest (NOI1), a translational readthrough motif (TRM), and a second nucleotide sequence of interest (NOI2), and
   a nucleotide sequence encoding a cleavage site (CL), so that NOI1 and NOI2 are expressed as separate proteins.

10. A nucleic acid construct comprising:
    a first nucleotide sequence of interest (NOI1), a translational readthrough motif (TRM), and a second nucleotide sequence of interest (NOI2), and
    a nucleotide sequence encoding a cleavage site (CL), so that NOI1 and NOI2 are expressed as separate proteins, wherein NOI2 encodes a cytokine, chemokine or toxin.

11. A vector comprising a nucleic acid according to claim 10.

12. A retroviral vector or a lentiviral vector according to claim 11.

13. A cell comprising a nucleic acid construct according to claim 10.

14. A method for making a cell according to claim 13 which comprises the step of introducing into a cell a nucleic acid construct comprising:
    a first nucleotide sequence of interest (NOI1), a translational readthrough motif (TRM), and a second nucleotide sequence of interest (NOI2), and
    a nucleotide sequence encoding a cleavage site (CL), so that NOI1 and NOI2 are expressed as separate proteins.

15. A nucleic acid construct comprising: a first nucleotide sequence of interest (NOI1), a translational readthrough motif (TRM) and a second nucleotide sequence of interest (NOI2),
    wherein the nucleic acid construct is capable of producing two products when expressed in a cell:
    a) a first product encoded by NOI1 alone, and
    b) a second product, encoded by NOI1 and NOI2, which is produced when translational readthrough occurs, and
    wherein the first and/or second product is a chimeric antigen receptor (CAR).

16. A nucleic acid construct according to claim 15, wherein the second product is a chimeric antigen receptor (CAR) and the first product is a truncated version of the CAR, incapable of inducing CAR-mediated cell signalling.

17. A nucleic acid construct according to claim 15, wherein the first product is a chimeric antigen receptor (CAR) comprising an intracellular signalling domain and the second product is a CAR comprising an intracellular signalling domain and one or more co-stimulatory domain(s).

18. A vector comprising a nucleic acid construct according to claim 15.

19. A retroviral vector or a lentiviral vector according to claim 18.

20. A cell comprising a nucleic acid construct according to claim 15.

21. A method for making a cell according to claim 20 which comprises the step of introducing into a cell a nucleic acid construct comprising:
    a first nucleotide sequence of interest (NOI1), a translational readthrough motif (TRM), and a second nucleotide sequence of interest (NOI2), and a nucleotide sequence encoding a cleavage site (CL), so that NOI1 and NOI2 are expressed as separate proteins.

* * * * *

UNITED STATES PATENT AND TRADEMARK OFFICE
CERTIFICATE OF CORRECTION

| | | |
|---|---|---|
| PATENT NO. | : 11,959,084 B2 | Page 1 of 1 |
| APPLICATION NO. | : 17/254001 | |
| DATED | : April 16, 2024 | |
| INVENTOR(S) | : Cordoba et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 645 days.

Signed and Sealed this
Eighth Day of October, 2024

Katherine Kelly Vidal
*Director of the United States Patent and Trademark Office*